United States Patent
Yue et al.

(10) Patent No.: US 11,597,753 B2
(45) Date of Patent: Mar. 7, 2023

(54) ACTIVATABLE IL2 COMPOSITION AND METHODS OF USE

(71) Applicant: Aetio Biotherapy, Inc., Dallas, TX (US)

(72) Inventors: Tao Yue, Coppell, TX (US); Yang Wang, Dallas, TX (US)

(73) Assignee: Immune Targeting, Inc., Dallas, TX (US)

( * ) Notice: Subject to any disclaimer, the term of this patent is extended or adjusted under 35 U.S.C. 154(b) by 27 days.

(21) Appl. No.: 17/245,679

(22) Filed: Apr. 30, 2021

(65) Prior Publication Data
US 2021/0340209 A1    Nov. 4, 2021

Related U.S. Application Data

(60) Provisional application No. 63/018,295, filed on Apr. 30, 2020.

(51) Int. Cl.
*C07K 14/55*    (2006.01)
*C07K 14/715*   (2006.01)

(52) U.S. Cl.
CPC .......... *C07K 14/55* (2013.01); *C07K 14/7155* (2013.01); *C07K 2319/30* (2013.01); *C07K 2319/32* (2013.01); *C07K 2319/33* (2013.01)

(58) Field of Classification Search
CPC ....................................................... C07K 14/55
See application file for complete search history.

(56) References Cited

U.S. PATENT DOCUMENTS

| 8,734,774 B2 | 5/2014 | Frelinger et al. |
| 2003/0229023 A1 | 12/2003 | Oliner et al. |
| 2016/0067316 A1 | 3/2016 | Sunavala-Dossabhoy |
| 2020/0040052 A1 | 2/2020 | Winston et al. |

FOREIGN PATENT DOCUMENTS

| WO | 2016/022671 A1 | 2/2016 |
| WO | 2020/057645 A1 | 3/2020 |
| WO | 2020/057646 A1 | 3/2020 |

OTHER PUBLICATIONS

Sun, et al. "A next-generation tumor-targeting IL-2 preferentially promotes tumor-infiltrating CD8+ T-cell response and effective tumor control" Nature Communications, (2019) 10:38741 https://doi.org/10.1038/s41467-019-11782-w, www.nature.com/naturecommunications.
United States Patent & Trademark Office (ISA), International Search Report and Written Opinion for PCT/US21/30190 dated Oct. 21, 2021, 13 pp.
Charych, et al. "NKTR-214, an Engineered Cytokine with Biased IL2 Receptor Binding, Increased Tumor Exposure, and Marked Efficacy in Mouse Tumor Models" Clin Cancer Res. Feb. 1, 2016;22(3):680-90. doi: 10.1158/1078-0432. CCR-15-1631.

*Primary Examiner* — Prema M Mertz
(74) *Attorney, Agent, or Firm* — Milstein Zhang & Wu LLC

(57) ABSTRACT

The present invention includes proteins, nucleic acids and methods of making and using an activatable interleukin-2 (aIL2) comprising an Interleukin-2 (aIL2) fusion protein comprising: an Interleukin-2 (IL2) wild-type or mutein; a first cleavable linker; an interleukin-2 receptor binding region (IL2RB), and a half-life extender, such as an antibody Fc region, wherein cleavage of the cleavable linker releases the IL2 from the interleukin-2 receptor beta binding region.

17 Claims, 15 Drawing Sheets

Specification includes a Sequence Listing.

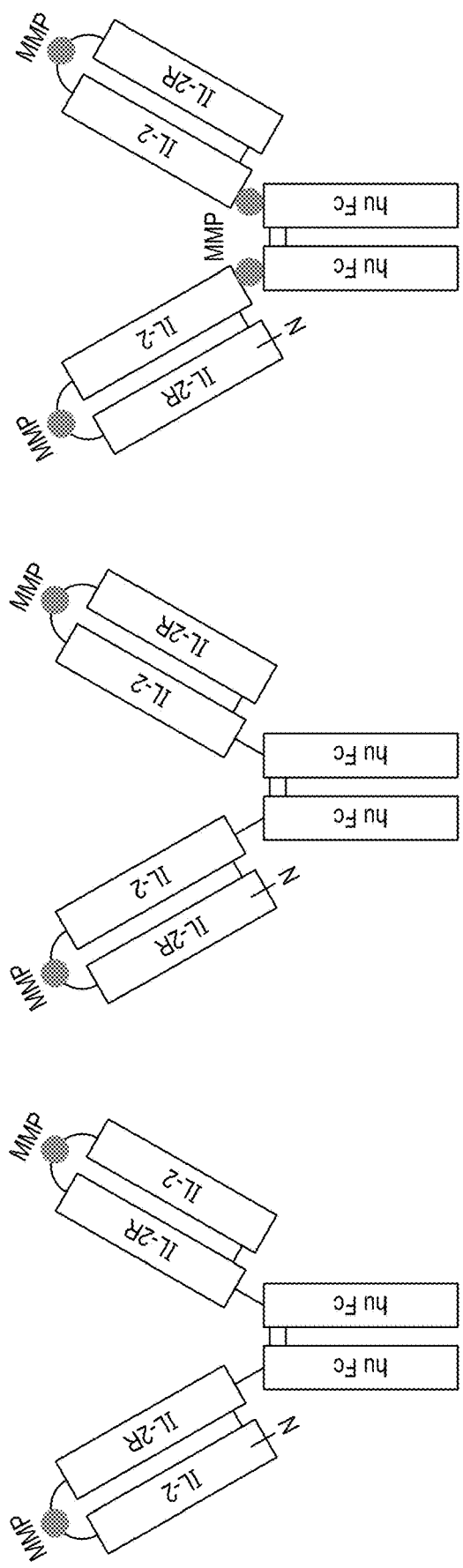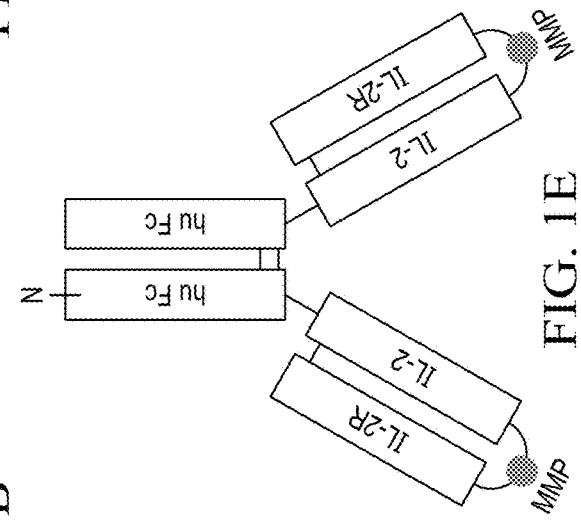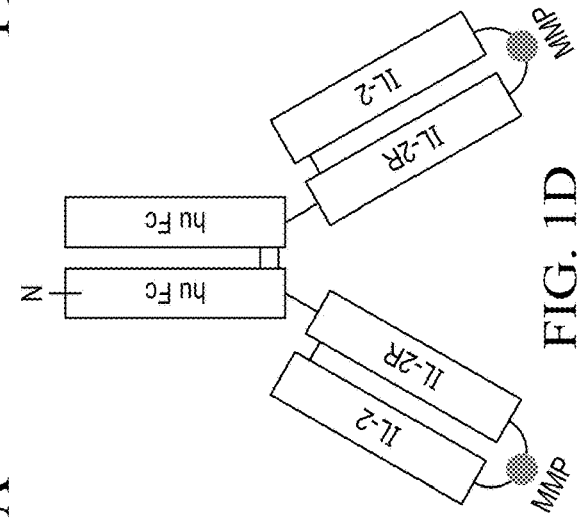

ACTIVATABLE IL2 COMPOSITION AND METHODS OF USE

CROSS-REFERENCE TO RELATED APPLICATIONS

This application claims priority to U.S. Provisional Application Ser. No. 63/018,295, filed Apr. 30, 2020, the entire contents of which are incorporated herein by reference.

TECHNICAL FIELD OF THE INVENTION

The present invention relates in general to the field of activatable interleukin-2 (IL2) constructs that reduce drug effects in normal tissue and enhance tumor targeting.

STATEMENT OF FEDERALLY FUNDED RESEARCH

Not applicable.

INCORPORATION-BY-REFERENCE OF MATERIALS FILED ON COMPACT DISC

The present application includes a Sequence Listing (TABLE) filed on a single compact disc (CD-R), filed in duplicate. The Sequence Listing is presented in a single file on each CD-R and is named AEBI1003_SL. The Sequence Listing was last modified Apr. 30, 2021 at 11:22 AM and includes 49,152 bytes.

BACKGROUND OF THE INVENTION

Without limiting the scope of the invention, its background is described in connection with interleukin-2 (IL2).

One such patent is international publication WO 2016/022671 A1, entitled, Interleukin-2/Interleukin-2 Receptor Alpha Fusion Proteins And Methods Of Use, and which is said to teach increasing activity of regulatory T cells (Tregs) and/or increasing immune tolerance in low dose IL2 based therapies; increasing immune response and memory in higher dose therapies; increasing IL2 availability when compared to recombinant IL2 through competitive interaction between IL2 with cells that express IL2R; and/or increasing persistent IL2 stimulation of IL2R bearing lymphocytes in vivo.

Another such patent is U.S. Pat. No. 8,734,774 B2, entitled, "Protease activated cytokines", which uses mouse IL2/PSAcs/linker/IL2Ralpha fusion protein and human IL2/PSAcs/linker/scFv (anti-human IL2) to reduce toxicity for the potential cancer therapy.

Yet other patent applications include international publications WO 2020/057646 A1 and WO 2020/057645 (CN2018101108649A), entitled "Novel Interleukin 2 And Use Thereof", that teach an IL2 mutant protein has a reduced IL-2a receptor binding capability and/or an improved IL2Rβ receptor binding capability. The fusion protein contains IL2 mutant protein, an immunoconjugate and a Fc peptide. These applications also teach an immunoconjugate that brings the IL2 mutant protein to the tumor site, and a Fc peptide increases the stability of IL2 mutant protein, and mutations in IL2 mutant protein abolished protein glycosylation, and subsequently reduced its binding to IL2Ra.

Finally, Charych, et al., in an article entitled "NKTR-214, an Engineered Cytokine with Biased IL2 Receptor Binding, Increased Tumor Exposure, and Marked Efficacy in Mouse Tumor Models" Clin Cancer Res. 2016 Feb. 1; 22(3):680-90. doi: 10.1158/1078-0432.CCR-15-1631, teaches preferential activation of IL2 receptor beta over receptor alpha using the location of PEG molecules to achieve such preferential activation.

What is needed are novel fusion proteins that overcome the problems in the prior art by eliminating targeting of normal tissues and enhancing the activity at the tumor target site, while also ensuring favorable properties of a biologic drugs such as increased half-life and ease of formulation and manufacturability.

SUMMARY OF THE INVENTION

In another embodiment, the present invention includes an activatable Interleukin-2 (aIL-2) fusion protein comprising: an Interleukin-2 (IL-2) wild type or IL-2 mutein; a first cleavable linker connected to the IL-2; an interleukin-2 receptor binding region (IL-2α or IL-2β receptor, interchangeable with IL-2RA or RB, respectively) connected to the first cleavable linker; and a half-life extender connected to the IL-2 or the IL-2 receptor, wherein cleavage of the cleavable linker releases the IL-2 from the IL-2 receptor. In one aspect, the half-life extender is an antibody Fc region, which is selected from: a wild-type Fc region, a mutated Fc region, a monomeric wild type Fc region, a monomeric mutant Fc region, a dimeric wild type Fc region, or a dimeric mutant Fc region. In another aspect, the cleavable linker is cleaved by a tumor associated protease. In another aspect, the cleavable linker is cleaved by a protease selected from matrix metallopeptidase-1 (MMP1), MMP2, MMP3, MMP7, MMP9, MMP10, MMP11, MMP12, MMP13, MMP14, MMP15, MMP16, MMP17, MMP19, MMP20, MMP21, uPA, FAPa, or Cathepsin B. In another aspect, the cleavable linker is cleaved by a caspase selected from Caspase 1, Caspase 2, Caspase 3, Caspase 4, Caspase 5, Caspase 6, Caspase 7, Caspase 8, Caspase 9, Caspase 10, Caspase 11 and Caspase 12. In another aspect, the cleavable linker is cleaved by matrix metallopeptidase 14. In another aspect, the IL-2 comprises one or more mutations that eliminate or reduce binding affinity to IL2RA or IL2RB. In another aspect, the IL-2 comprises one or more mutations selected from: F42A, K, R, E, or Q; Y45A, K, R, E, Q, F, W, or H; L72A, G, K, R, E, or Q; R81A, H, K, D, E, N, or Q; L85A, I, G, K, R, E, Q, T, or S; I86A, I, G, K, R, E, Q, T, or S. In another aspect, the IL-2 is mutated to increase binding affinity to IL2RB. In another aspect, the fusion protein is a homodimer. In another aspect, the fusion protein is a heterodimer. In another aspect, the fusion protein further comprises a target-binding polypeptide, wherein the target is selected from HER1, HER2, HER3, GD2, carcinoembryonic antigens (CEAs), epidermal growth factor receptor active mutant (EGFRVIII), CD133, Fibroblast Activation Protein Alpha (FAP), Epithelial cell adhesion molecular (Epcam), Glypican 3 (GPC3), EPH Receptor A4 (EphA), tyrosine-protein kinase Met (cMET), IL-13Ra2, microsomal epoxide hydrolase (mEH), MAGE, Mesothelin, MUC16, MUC1, prostate stem cell antigen (PSCA), Wilms tumor-1 (WT-1), a Claudin family protein; a T-cell marker selected from CTLA-4, PD-1, Lag3, S15, B7H3, B7H4, TCR-alpha, TCR-beta, TIM-3, CD3, 41BB or OX40; and/or an antigen-presenting cell marker selected from PD-L1, CD40, CD24, B7H3, TGF-beta receptor, TNFR family members 1 to 20, CD80, CD86, FLT3, CD11c, CD8-alpha, 5B6 (CLEC9A), CD1c, CD11b, CD13, CD33, HLA-DR, CD141, CD1a, CD32, CD45, CD80, CD86, CD207, CD2, CD7, CD45RA, CD68, CD123, CD303, CD304. In another aspect, the fusion protein reduces the in vivo toxicity of the aIL-2 when compared to IL-2. In another aspect, the fusion protein comprises, in order, the IL-2, the first cleavable linker, the IL-2 receptor, and a mutant antibody Fc region; the fusion protein comprises, in order, IL-2 receptor, the first cleavable linker, the IL-2, and the antibody Fc region; the fusion protein comprises, in order, the IL-2 or the IL-2 receptor, the first cleavable linker, the IL-2 or the IL-2 receptor, a second cleavable linker, and the antibody Fc region; the fusion protein comprises, in order, the antibody Fc region, the first cleavable linker, an IL-2 receptor, the second cleavable linker, and the IL-2; or the fusion protein comprises, in order, the antibody Fc region, the IL-2 receptor, the first cleavable linker, and the IL-2. In another aspect, the cleavable linker is a protease cleavable linker. In another aspect, the cleavable linker is cleaved by proteases upregulated during apoptosis or inflammation associated responses. In another aspect, the aIL-2 has a wild-type or mutant IL-2 selected from SEQ ID NOS: 1 to 10. In another aspect, the fusion protein comprises: (a) IL-2 is SEQ ID NOS: 1-10; (b) the IL-2Rα (SEQ ID NO:20) or the IL-2Rβ (SEQ ID NO: 21); (c) the cleavable linker is selected from SEQ ID NOS: 11-13, (d) human IgG1-Fc is SEQ ID NOS:14-19; and optionally a target-binding polypeptide. In another aspect, the aIL-2 has reduced toxicity in the heart, lungs, kidneys, or central nervous system when compared to IL-2. In another aspect, at least one of: the Interleukin-2 (IL-2); the first cleavable linker; the interleukin-2 receptor binding region (IL-2α or β receptor), or the antibody Fc region is a human sequence.

In another embodiment, the present invention includes a pharmaceutical composition comprising an activatable Interleukin-2 (aIL-2) fusion protein comprising: an Interleukin-2 (IL-2) wild type or mutein; a first cleavable linker connected to the IL-2; an interleukin-2 receptor binding region (IL-2α or IL-2β receptor) connected to the first cleavable linker; and a half-life extender connected to the IL-2 or the IL-2 receptor, wherein cleavage of the cleavable linker releases the IL-2 from the IL-2 receptor and a carrier.

In another embodiment, the present invention includes a method of reducing binding activity of an activatable Interleukin-2 (aIL-2) against normal tissues and targeting a cancer cell comprising administering an effective amount an activatable Interleukin-2 (aIL-2) fusion protein comprising: an Interleukin-2 (IL-2) wild type or mutein; a first cleavable linker connected to the IL-2; an interleukin-2 receptor binding region (IL-2α or IL-2β receptor) connected to the first cleavable linker; and a half-life extender connected to the IL-2 or the IL-2 receptor, wherein cleavage of the cleavable linker releases the IL-2 from the IL-2 receptor to a subject in need thereof.

In another embodiment, the present invention includes method of treating, alleviating a symptom of, or delaying the progression of a cancer comprising administering an effective amount of the antibody of claim 1 to a subject in need thereof. In one aspect, the cancer is a cancer that expresses an enzyme that cleaves the cleavable linker. In another aspect, the cancer is selected from a bladder cancer, a bone cancer, a breast cancer, a carcinoid, a cervical cancer, a colon cancer, an endometrial cancer, a glioma, a head and neck cancer, a liver cancer, a lung cancer, a lymphoma, a melanoma, an ovarian cancer, a pancreatic cancer, a prostate cancer, a renal cancer, a sarcoma, a skin cancer, a stomach cancer, a testis cancer, a thyroid cancer, a urogenital cancer, or a urothelial cancer. In another aspect, the cancer is selected from the group consisting of: acute myeloid leukemia, adrenocortical carcinoma, B-cell lymphoma, bladder urothelial carcinoma, breast ductal carcinoma, breast lobular carcinoma, carcinomas of the esophagus, castration-resistant prostate cancer (CRPC), cervical carcinoma, cholangiocarcinoma, chronic myelogenous leukemia, colorectal adenocarcinoma, colorectal cancer (CRC), esophageal carcinoma, gastric adenocarcinoma, glioblastoma multiforme, head and neck squamous cell carcinoma, Hodgkin's lymphoma/primary mediastinal B-cell lymphoma, hepatocellular carcinoma (HCC), kidney chromophobe carcinoma, kidney clear cell carcinoma, kidney papillary cell carcinoma, lower grade glioma, lung adenocarcinoma, lung aquamous cell carcinoma, melanoma (MEL), mesothelioma, non-squamous NSCLC, ovarian serous adenocarcinoma, pancreatic ductal adenocarcinoma, paraganglioma & pheochromocytoma, prostate adenocarcinoma, renal cell carcinoma (RCC), sarcoma, skin cutaneous melanoma, squamous cell carcinoma of the head and neck, T-cell lymphoma, thymoma, thyroid papillary carcinoma, uterine carcinosarcoma, uterine corpus endometrioid carcinoma and uveal melanoma.

BRIEF DESCRIPTION OF THE DRAWINGS

For a more complete understanding of the features and advantages of the present invention, reference is now made to the detailed description of the invention along with the accompanying figures and in which:

FIGS. 1A to 1J show Pro-IL2 with or without target-binding polypeptide. FIGS. 1A to 1E, show schematic diagrams of pro-IL-2 homodimer protein drugs. IL-2 WT or muteins with altered binding affinity to IL-2R with changed or unchanged pH, is linked to IL-2R alpha or beta with tumor tissue-specific cleavage site, either followed or preceded by a half-life extender, such as human Fc. Examples include (FIG. 1A) $IL2_{wt\ or\ mu}$-MMP-$IL2R_\alpha$ or $_\beta$-$hFc_{wt}$ or $_{mu}$, (FIG. 1B) $IL2R_\alpha$ or $_\beta$-MMP-$IL2_{wt}$ or $_{mu}$-$hFc_{wt}$ or $_{mu}$, (FIG. 1C) $IL2R_\alpha$ or $_\beta$-MMP-$IL2_{wt}$ or $_{mu}$-MMP-$hFc_{wt}$ or $_{mu}$, (FIG. 1D) $hFc_{wt}$ or $_{mu}$-$IL2R_\alpha$ or $_\beta$-MMP-$IL2_{wt}$ or $_{mu}$, (FIG. 1E) $hFc_{wt}$ or $_{mu}$-$IL2_{wt}$ or $_{mu}$-MMP-$IL2R_\alpha$ or $_\beta$. FIGS. 1F to 1J show schematic diagrams of pro-IL-2 homodimer protein drugs, fused with two target-binding polypeptides or one target-binding polypeptide. Examples include (FIG. 1F) $IL2_{wt}$ or $_{mu}$-MMP-$IL2R_\alpha$ or $_\beta$-$hFc_{wt}$ or $_{mu}$-target-binding polypeptide, (FIG. 1G) $IL2R_\alpha$ or $_\beta$-MMP-$IL2_{wt}$ or $_{mu}$-$hFc_{wt}$ or $_{mu}$-target-binding polypeptide, (FIG. 1H) $IL2R_\alpha$ or $_\beta$-MMP-$IL2_{wt}$ or $_{mu}$-MMP-$hFc_{wt}$ or $_{mu}$-target-binding polypeptide, (FIG. 1I) target-binding polypeptide-$hFc_{wt}$ or $_{mu}$-$IL2R_\alpha$ or $_\beta$-MMP-$IL2_{wt}$ or $_{mu}$, and (FIG. 1J) target-binding polypeptide-$hFc_{wt}$ or $_{mu}$-$IL2_{wt}$ or $_{mu}$-MMP-$IL2R_\alpha$ or $_\beta$.

FIGS. 2A to 2E, show schematic diagrams of pro-IL-2 heterodimer protein drugs. IL-2 WT or muteins with lower affinity, or higher affinity, or pH resistance, is linked to IL-2R alpha or beta with tumor tissue-specific cleavage site, either followed or preceded by a half-life extender, as part of the heterodimer. The other part includes target-binding polypeptide-fused half-life extender to form a heterodimer. Examples include (FIG. 2A) $IL2_{wt}$ or $_{mu}$-MMP-$IL2R_\alpha$ or $_\beta$-hFc6mu, (FIG. 2B) $IL2R_\alpha$ or $_\beta$-MMP-$IL2_{wt}$ or $_{mu}$-hFc6mu, (FIG. 2C) $IL2R_\alpha$ or $_\beta$-MMP-$IL2_{wt}$ or $_{mu}$-MMP-hFc6mu, (FIG. 2D) hFc6mu-$IL2R_\alpha$ or $_\beta$-MMP-$IL2_{wt\ or\ mu}$, (FIG. 2E) hFc6mu-$IL2_{wt}$ or $_{mu}$-MMP-$IL2R_\alpha$ or $_\beta$. hFc6mu is dimerized with hFc9mu arm carrying the targeting correspond antibody. hFc6mu and hFc9mu positions are interchangeable. FIGS. 2F to 2G show IL-2 WT or muteins, and IL-2R alpha or beta, are fused to different Fc either at its N terminus or C terminus to form heterodimers. Antigen binding polypeptide is fused to the other side of Fc. Examples include (FIG. 2F) IL2R$_\alpha$ or $_\beta$-MMP- hFc6mu-antigen binding polypeptide, dimerized with IL2$_{wt\,or\,mu}$-hFc9mu-antigen binding polypeptide, (FIG. 2G) antigen binding polypeptide-hFc6mu-MMP-IL2R$_\alpha$ or $_\beta$, dimerized with antigen binding polypeptide-hFc9mu-IL2$_{wt}$ or $_{mu}$. hFc6mu and hFc9mu positions are interchangeable.

(FIG. 3A) Flow cytometry data shows that IL-2R beta at a series of concentrations, binds to yeast expressing IL-2 mutein more strongly than IL-2 WT. (FIG. 3B) ELISA data shows that IL-2R beta binds to IL-2 mutein about 20 times stronger than IL-2 WT. The IL-2 mutein protein sequence is indicated in SEQ ID NO:3.

(FIG. 4A) Flow cytometry data shows that IL-2R beta at a series of concentrations, binds to yeast expressing IL-2 mutein more strongly than IL-2 WT at pH6.9. (FIG. 4B) ELISA data shows that IL-2R beta binds to IL-2 mutein, but not WT at pH 6.4, when both contains IL-2 mutein and WT contains F42A mutation to eliminate the binding to IL-2R alpha. The IL-2 mutein protein sequences are indicated in SEQ ID NOS:3-4.

(FIG. 5A) ELISA data shows that IL-2 mutein induces human PBMC to produce IFN gamma about 10 times more strongly than IL-2 WT protein, when co-stimulated with anti-CD3 antibody. By contrast, the activity of IL-2 mutein pro-drug is more than 15 times lower than IL-2 WT, and more than 1000 times lower than IL-2 mutein. (FIG. 5B) ELISA data shows that IL-2 mutein pro-drug restores its activity to activate human PBMC for IFN gamma production after removal of the blocking moiety by incubating with MMP14 protein, when co-stimulated with anti-CD3 antibody. The IL-2 mutein protein sequences are indicated in SEQ ID NO:3.

(FIG. 6) pro-IL-2 mutein drug significantly inhibits tumor growth in the humanized mouse model with mild body weight loss and improved survival, compared with IL-2 treatment. NSG-SGM3 mice inoculated with MDA-MB-231, followed by huPBMC transfer, and the treatment with IL-2 or pro-IL-2 mutein drugs. The IL-2 mutein protein sequences are indicated in SEQ ID NO:3. (FIG. 7) compared with hIgG and target-binding polypeptide-fused unrelated protein, target-binding polypeptide-fused IL-2 prodrug significantly inhibits tumor growth in mouse Antigen+M38 tumor model. The protein sequences of target-binding polypepetide-fused pro-IL-2 muteins are indicated in SEQ ID NOS:23-24.

DETAILED DESCRIPTION OF THE INVENTION

Figure 1H:
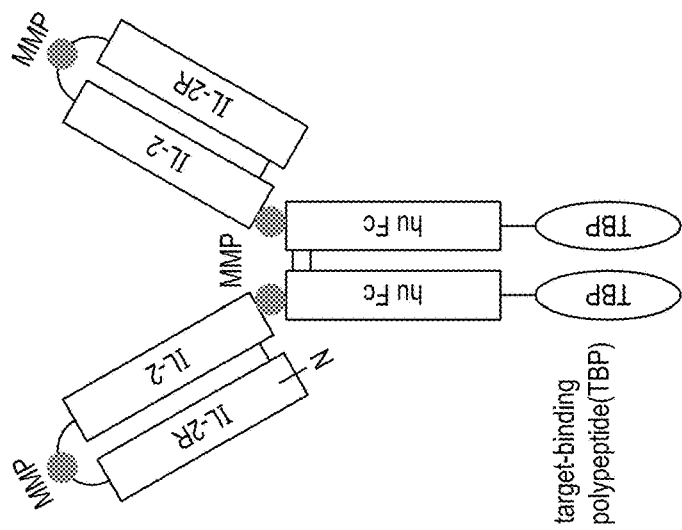
Figure 1G:
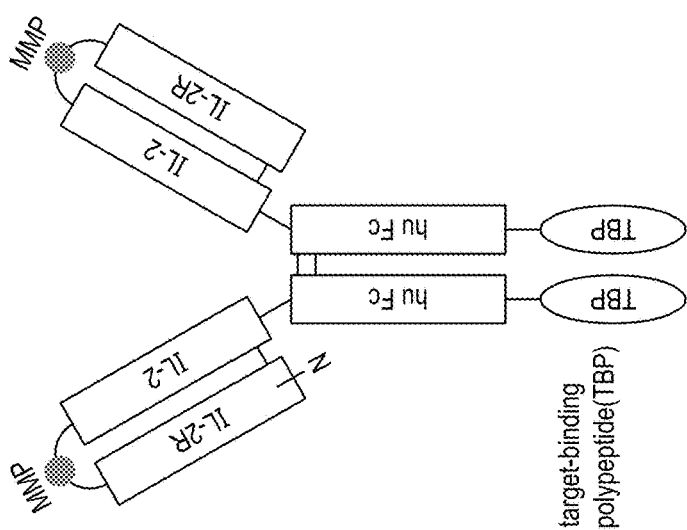
Figure 1F:
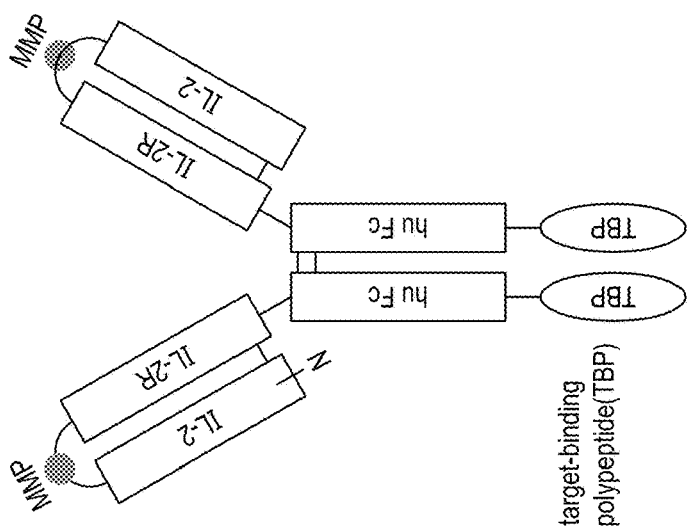
Figure 1J:
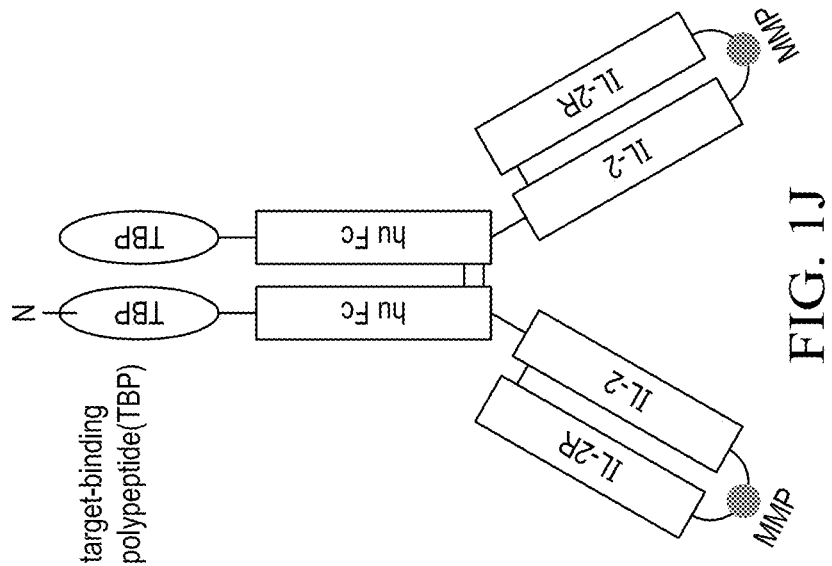
Figure 1I:
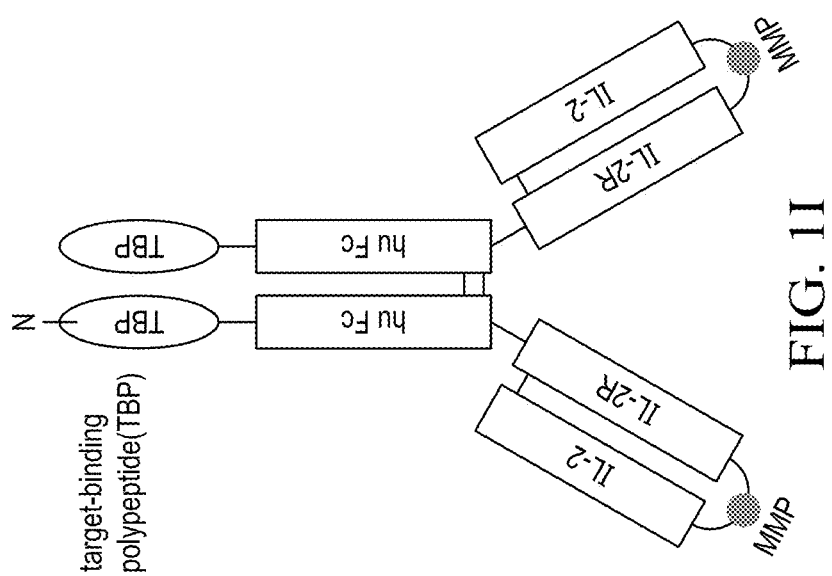

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but include the general class of which a specific example may be used for illustration. The terminology herein is used to describe specific embodiments of the invention, but their usage does not limit the invention, except as outlined in the claims.

High-dose Interleukin-2 (IL2), used in the treatment of cancers, is associated with significant side effects due to short half-life and its toxicity in multiple organ systems, including the heart, lungs, kidneys, and central nervous system. It is critical to specifically activate IL2 activity preferentially in the tumor microenvironment and much less in other tissues to reduce its toxicity. The present inventors have designed an IL2 prodrug, which is an activatable IL2, by using IL2 receptor beta to block its activity in the normal tissue. The IL2 receptor beta is removed by cleavage of a linker that is susceptible to enzymes or other factors in the tumor microenvironment. One example of a cleavable linker is a peptide linker, e.g., an MMP14 peptide substrate sequence that is cleaved in site in a tumor microenvironment in which MMP14 is found or enriched.

The present invention reduces off-target toxicities for monoclonal antibody therapies, thereby increasing the therapeutic index and drug tolerability for patients by linking the extracellular domain of IL2RB to IL2 and increasing the binding affinity of IL2 to IL2RB over IL2RA. The close proximity of IL2 and IL2RB by using a short, cleavable linker allows IL2B to block IL2 in vitro and in vivo until the drug reaches the tumor site where proteases that can cleave the linker are often upregulated. In the present invention, the extracellular domain (ECD) of ILRB is used to block IL2, which are connected via a peptide linker, such as an MMP peptide and/or an MMP-based peptide linker. It was found that the activatable IL2 taught herein have little to no activity until the drug reaches the tumor, thus yielding a long half-life, protein stability and manufacturability. The new activatable IL2 constructs also feature mutations that reduce the binding affinity of IL2 to IL2RA, further increasing its ability to bind to effector T cells within tumor tissues while avoiding T reg.

The present invention reduces off-target toxicities for monoclonal antibody therapies, thereby increasing the therapeutic index and drug tolerability for patients by linking the extracellular domain of IL2RA to IL2 WT or mutein in which mutations increases the binding affinity of IL2 to IL2RB. The close proximity of IL2 and IL2RA by using a short, cleavable linker allows IL2A to block IL2 in vitro and in vivo until the drug/fusion protein reaches the tumor site where proteases that can cleave the linker are often upregulated. In the present invention, the extracellular domain (ECD) of ILRA is used to block IL2, which are connected via a peptide linker, such as an MMP peptide and/or an MMP-based peptide linker. It was found that the activatable IL2 taught herein have minimal to no activity until the drug reaches the tumor, thus yielding a long half-life, protein stability and manufacturability. The new activatable IL2 constructs also feature mutations that increases the binding affinity of IL2 to IL2RB, further increasing its ability to activate T cells within tumor tissues while avoiding Treg.

As used herein, the term "activatable IL2", "aIL2", or "pro-IL2" refers to a fusion protein that includes an IL2 and an IL2 receptor (IL-2α or IL-2β receptor) separated by a cleavable linker.

A nucleic acid encoding the aIL2 can be part of a vector that is used to express the aIL2 in a host cell, such as a bacterial, fungal, plant, or mammalian cell.

As used herein, the phrase "increased half-life" and "half-life extender" refers to a portion of the fusion protein that will increase the half-life of the protein when introduced into a subject. Typically, the half-life of a protein is measured as a serum half-life, which is the amount of time during which 50% of a protein is removed from circulation. For example, certain mutations to the antibody Fc domain are known to significantly increase the serum half-life of the protein and can be used to increase the half-life of the fusion proteins of the present invention.

In certain embodiments, the prodrug IL2 sequence contains one or mutations from the group of F42A, K, R, E, Q; Y45A, K, R, E, Q, F, W, H; L72A, G, K, R, E, to reduce binding to IL2 receptor alpha. In some embodiments, the IL2 sequence has one or more mutations from the group of R81A, H, K, D, E, N, Q; L85A, I, G, K, R, E, Q, T, S; I86A, I, G, K, R, E, Q, T, S; to increase binding affinity to IL2 receptor beta. One example of an IL2 featuring increased affinity to IL2RB for use with the present invention is taught in U.S. Pat. No. 10,150,802, relevant sequences incorporated herein by reference.

In additional embodiments, the IL2 sequence contains either wild-type sequence or one or more mutations. In some embodiments the IL2 prodrug is a homodimer Fc construct. In yet other embodiments, the antigen binding domain is attached to the N'-terminal of the Fc region. In some embodiments, the antigen binding domain is attached to the C'-terminal of Fc.

As used herein, the phrase "target-binding polypeptide" refers to peptides or polypeptides that specifically bind a biological target, e.g., a ligand that binds to its cognate receptor, or an antibody binds to its specific antigen, which can be a protein, carbohydrate, nucleic acid, lipid, small molecule, etc. Examples of target-binding polypeptides also include antibodies against tumor cell-specific antigen, T cell-specific antigen, and protein specifically residing in the tumor tissues, and the antibodies could be antibody Fab, scFab, scFv.

In some embodiments, the IL2 prodrug is a heterodimer Fc key and knob construct wherein the Fc6 (key) arm carries the IL2 prodrug and Fc9 (key) arm carries the target-binding polypeptide, which can be, e.g., a targeting antibody. In some embodiments, the target-binding polypeptide binds to a tumor targeting antigen selected from HER1, HER2, HER3, GD2, carcinoembryonic antigens (CEAs), epidermal growth factor receptor active mutant (EGFRVIII), CD133, Fibroblast Activation Protein Alpha (FAP), Epithelial cell adhesion molecular (Epcam), Glypican 3 (GPC3), EPH Receptor A4 (EphA), tyrosine-protein kinase Met (cMET), IL-13Ra2, microsomal epoxide hydrolase (mEH), MAGE, Mesothelin, MUC16, MUC1, prostate stem cell antigen (PSCA), Wilms tumor-1 (WT-1), or a Claudin family protein.

In some embodiments, the target-binding polypeptide binds to a T-cell marker selected from CTLA-4, PD-1, Lag3, S15, B7H3, B7H4, TCR-alpha, TCR-beta, or TIM-3, CD3, 41BB or OX40.

In some embodiments, the target-binding polypeptide binds to an antigen-presenting cell marker selected from PD-L1, CD40, CD24, B7H3, TGF-beta receptor, TNFR family members 1 to 20, CD80, CD86, FLT3, CD11e, CD8-alpha, 5B6 (CLEC9A), CD1c, CD11b, CD13, CD33, HLA-DR, CD141, CD1a, CD32, CD45, CD80, CD86, CD207, CD2, CD7, CD45RA, CD68, CD123, CD303, CD304.

As used herein, the terms "Fc antibody region mutant" or "mutant Fc" refer to an amino acid sequence variant of an antibody wherein one or more of the amino acid residues have been modified, e.g., mutations in the Fc portion of the antibody. Such mutants necessarily have less than 100% sequence identity or similarity with the amino acid sequence having at least 75% amino acid sequence identity or similarity with the amino acid sequence of either the heavy or light chain variable domain of the antibody, such as at least 80%, or at least 85%, or at least 90%, or at least 95, 96, 97, 98, or 99%. The purpose of mutating the Fc region is to reduce or eliminate ADCC function or prevent dimerization, thus forming a monomeric Fc antibody.

Depending on the amino acid sequences "immunoglobulins" can be assigned to different classes. There are at least five (5) major classes of immunoglobulins: IgA, IgD, IgE, IgG and IgM, and several of these may be further divided into subclasses (isotypes), e.g., IgG-1, IgG-2, IgG-3 and IgG4; IgA-1 and IgA-2. The subunit structures and three-dimensional configurations of different classes of immunoglobulins are well known. The present invention can use Fc regions of any isotype.

The present invention also includes cleavable linkers, such as protease cleavable linkers. Examples of cleavable linker are peptides that include sequences cleaved by a tumor associated protease: MMP1, MMP2, MMP3, MMP7, MMP9, MMP10, MMP11, MMP12, MMP13, MMP14, MMP15, MMP16, MMP17, MMP19, MMP20, MMP21, uPA, FAPa, or Cathepsin B. Other examples include a cleavable linker that is cleaved by proteases upregulated during apoptosis or inflammation associated responses, or when a subject is receiving radiation therapy, e.g., a caspase. Examples of caspases are Caspase 1, Caspase 2, Caspase 3, Caspase 4, Caspase 5, Caspase 6, Caspase 7, Caspase 8, Caspase 9, Caspase 10, Caspase 11, and/or Caspase 12.

The aIL2 design of the present invention. To avoid off-target IL2 interactions, the present invention reduces or blocks the IL2 from binding its target receptor on cell surfaces by blocking the IL2 with an IL2 binding region, e.g., an IL2 receptor beta binding region, separated by a cleavable linker. After the cleavable linker is cut at the target site, the IL2 is released from the IL2 receptor binding region and IL2 is released locally with its complete binding ability.

IL-2 muteins for use with the present invention abolish or reduce the binding to IL2R alpha with altered binding to receptor beta, which activates the effector T cells in tumor microenvironment without activating regulatory T cells highly expressing receptor alpha. This has the potential to exhibit enhanced tumor-killing activity. To alter IL-2 binding to its receptor alpha and beta and minimize its adverse effect, IL-2 muteins contain amino acid substitutions at the following positions of human IL-2 (SEQ ID NO:1) including one or more substitutions, selected from F42A, K, R, E, or Q; Y45A, K, R, E, Q, F, W, or H; L72A, G, K, R, E, or Q; R81A, H, K, D, E, N, or Q; L85A, I, G, K, R, E, Q, T, or S; I86A, I, G, K, R, E, Q, T, or S.

MMP14 cleavage sequence is embedded in the linker region which connects IL2R and IL2. This allows IL2R-mediated blockage in MMP14-positive tumors.

In addition to the F42A substitution in the IL2 mutein, which decreases binding to receptor alpha, mutations that increase the binding to IL2 receptor beta and enhance the efficacy of prodrug are also included. The huFc region greatly increases the half-life of pro-drug, allows for convenient purification by affinity columns, and improves production stability. In certain embodiments, mutant Fc regions that cannot bind to FcR on phagocytes can be used to reduce the depletion of effector cells.

In certain embodiments, the pro-IL2 of the present invention includes four basic modular domains: a half-life extender (such as hFc WT or its mutant), IL2 wild type or IL2 mutein, IL2 receptor alpha or beta, and protease cleavable linker. To increase the in vivo half-life of IL2, it is possible to conjugate IL2 to hIgG1 Fc-mu, which increases IL2 stability in the serum, and has no antibody-dependent cellular cytotoxicity (ADCC). To increase IL2 activation of CD8 T cells and NKs over Tregs, one or more mutations were introduced (F42A) into IL2 that reduce or abolish IL2 affinity for receptor alpha, and then also create other novel IL2 mutations, which alter the affinity of IL2 to IL2R beta at the neural or lower pH. To minimize the peripheral toxicity, IL2 activity is blocked with IL2 receptor beta. To target IL2 activity to the tumor microenvironment (TME), IL2 is linked with the IL2 receptor beta with a linker that is cleavable by a tumor specific protease, MMP14. Because MMP14 is specifically expressed in the TME, cleaving pro-IL2 at an MMP14 cleavage site allows the soluble IL2R beta to dissociate from IL2 mutein and restores IL2 activity in the TME.

FIGS. 1A to 1J show Pro-IL2 with or without target-binding polypeptide. FIGS. 1A to 1E, show schematic diagrams of pro-IL-2 homodimer protein drugs. IL-2 WT or muteins with altered binding affinity to IL-2R with changed or unchanged pH, is linked to IL-2R alpha or beta with tumor tissue-specific cleavage site, either followed or preceded by a half-life extender, such as human Fc. Examples include (FIG. 1A) $IL2_{wt}$ or $_{mu}$-MMP-$IL2R_\alpha$ or $_\beta$-$hFc_{wt}$ or $_{mu}$, (FIG. 1B) $IL2R_\alpha$ or $_\beta$-MMP-$IL2_{wt}$ or $_{mu}$-$hFc_{wt}$ or $_{mu}$, (FIG. 1C) $IL2R_\alpha$ or $_\beta$-MMP-$IL2_{wt}$ or $_{mu}$-MMP-$hFc_{wt}$ or $_{mu}$, (FIG. 1D) $hFc_{wt}$ or $_{mu}$-$IL2R_\alpha$ or $_\beta$-MMP-$IL2_{wt}$ or $_{mu}$, (FIG. 1E) $hFc_{wt}$ or $_{mu}$-$IL2_{wt}$ or $_{mu}$-MMP-$IL2R_\alpha$ or $_\beta$. FIGS. 1F to 1J show schematic diagrams of pro-IL-2 homodimer protein drugs, fused with two target-binding polypeptides or one target-binding polypeptide. Target-binding polypeptide include antibodies against tumor cell-specific antigen, T cell-specific antigen, and protein specifically residing in the tumor tissues, and the antibodies could be antibody Fab, scFab, scFv. Examples include (FIG. 1F) $IL2_{wt}$ or $_{mu}$-MMP-$IL2R_\alpha$ or $_\beta$-$hFc_{wt}$ or $_{mu}$-target-binding polypeptide, (FIG. 1G) $IL2R_\alpha$ or $_\beta$-MMP-$IL2_{wt}$ or $_{mu}$-$hFc_{wt}$ or $_{mu}$-target-binding polypeptide, (FIG. 1H) $IL2R_\alpha$ or $_\beta$-MMP-$IL2_{wt}$ or $_{mu}$-MMP-$hFc_{wt}$ or $_{mu}$-target-binding polypeptide, (FIG. 1I) target-binding polypeptide-$hFc_{wt}$ or $_{mu}$-$IL2R_\alpha$ or $_\beta$-MMP-$IL2_{wt}$ or $_{mu}$, and (FIG. 1J) target-binding polypeptide-$hFc_{wt}$ or $_{mu}$-$IL2_{wt}$ or $_{mu}$-MMP-$IL2R_\alpha$ or $_\beta$.

Figure 2A:
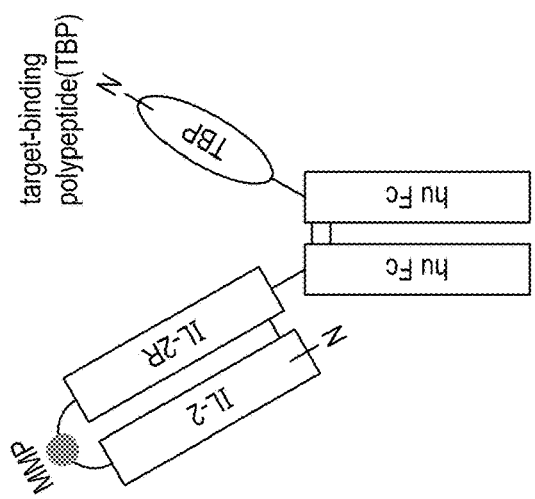
FIG. 2A to 2G show heterodimer of pro-IL2 x tumor targeting polypeptide.
Figure 2B:
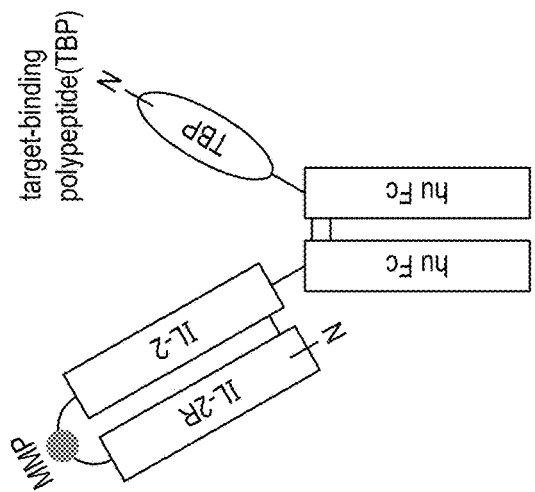
Figure 2C:
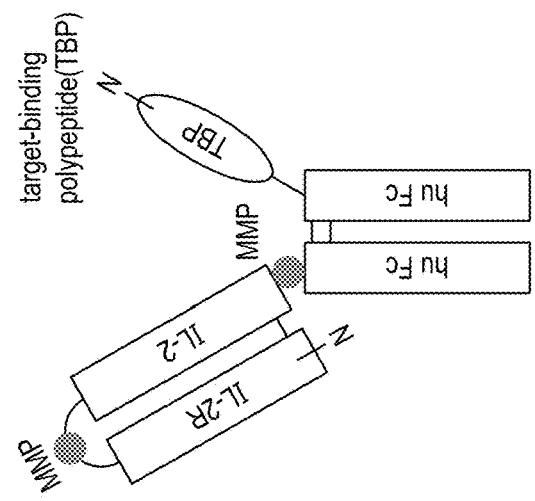
Figure 2E:
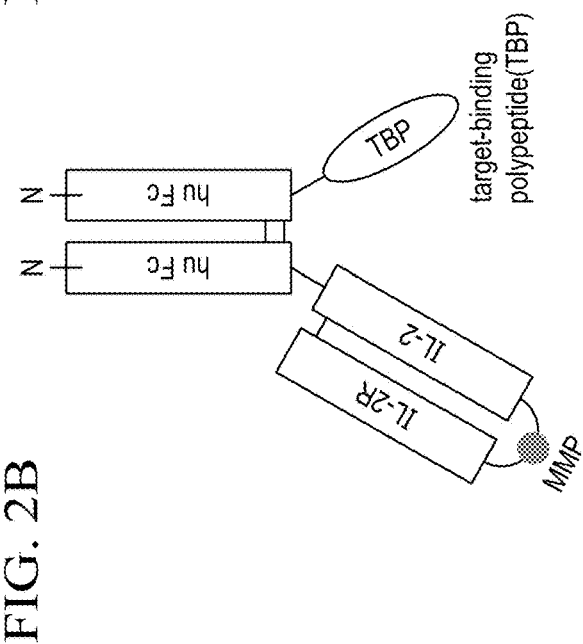
Figure 2D:
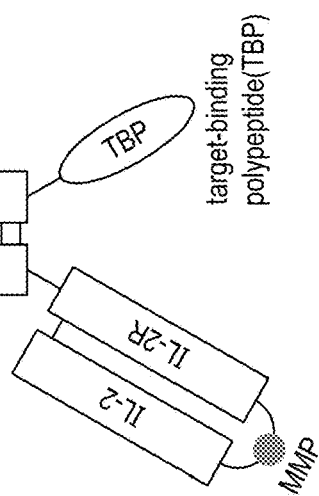
Figure 2G:
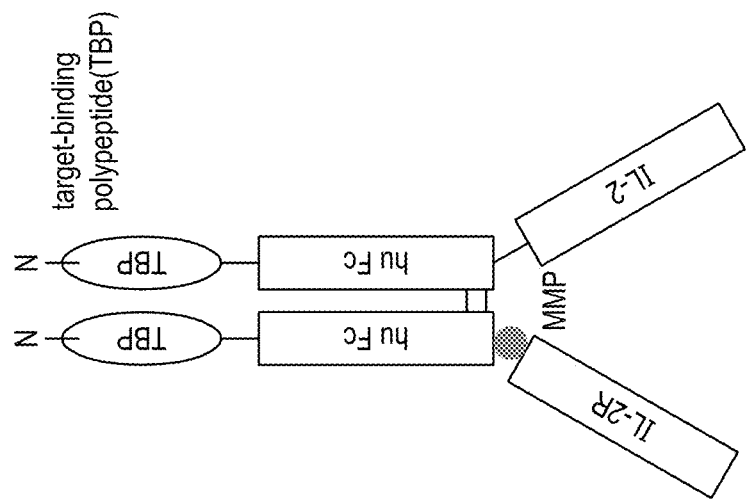
Figure 2F:
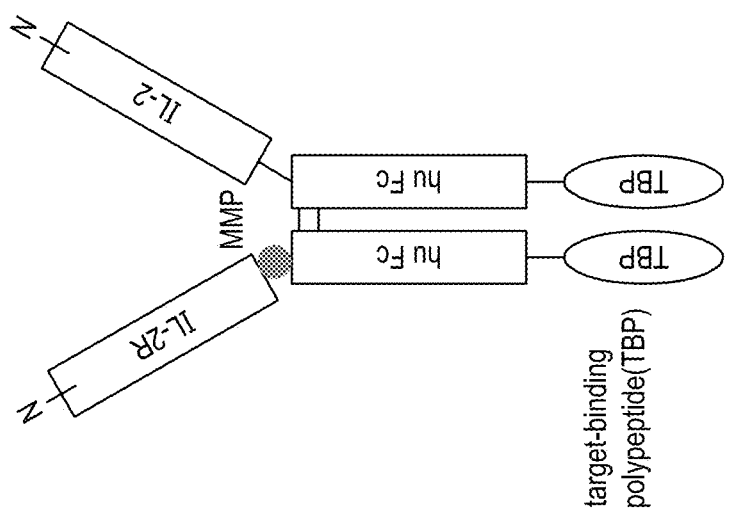

FIG. 2A to 2G show heterodimer of pro-IL2 x tumor targeting polypeptide. FIGS. 2A to 2E, show schematic diagrams of pro-IL-2 heterodimer protein drugs. IL-2 WT or muteins with lower affinity, or higher affinity, or pH resistance, is linked to IL-2R alpha or beta with tumor tissue-specific cleavage site, either followed or preceded by a half-life extender, as part of the heterodimer. The other part includes target-binding polypeptide-fused half-life extender to form a heterodimer. Examples include (FIG. 2A) $IL2_{wt}$ or $_{mu}$-MMP-$IL2R_\alpha$ or $_\beta$-hFc6mu, (FIG. 2B) $IL2R_\alpha$ or $_\beta$-MMP-$IL2_{wt}$ or $_{mu}$-hFc6mu, (FIG. 2C) $IL2R_\alpha$ or $_\beta$-MMP-$IL2_{wt}$ or $_{mu}$-MMP-hFc6mu, (FIG. 2D) hFc6mu-$IL2R_\alpha$ or $_\beta$-MMP-$IL2_{wt}$ or $_{mu}$, (FIG. 2E) hFc6mu-$IL2_{wt}$ or $_{mu}$-MMP-$IL2R_\alpha$ or $_\beta$. hFc6mu is dimerized with hFc9mu arm carrying the targeting correspond antibody. hFc6mu and h Fc9mu positions are interchangeable. FIGS. 2F to 2G show IL-2 WT or muteins, and IL-2R alpha or beta, are fused to different Fc either at its N terminus or C terminus to form heterodimers. Antigen binding polypeptide is fused to the other side of Fc. Examples include (FIG. 2F) $IL2R_\alpha$ or $_\beta$-MMP-hFc6mu-antigen binding polypeptide, dimerized with $IL2_{wt}$ or $_{mu}$-hFc9mu- antigen binding polypeptide, (FIG. 2G) antigen binding polypeptide-hFc6mu-MMP-$IL2R_\alpha$ or $_\beta$, dimerized with antigen binding polypeptide-hFc9mu-$IL2_{wt}$ or $_{mu}$. hFc6mu and hFc9mu positions are interchangeable.

Figure 3A:
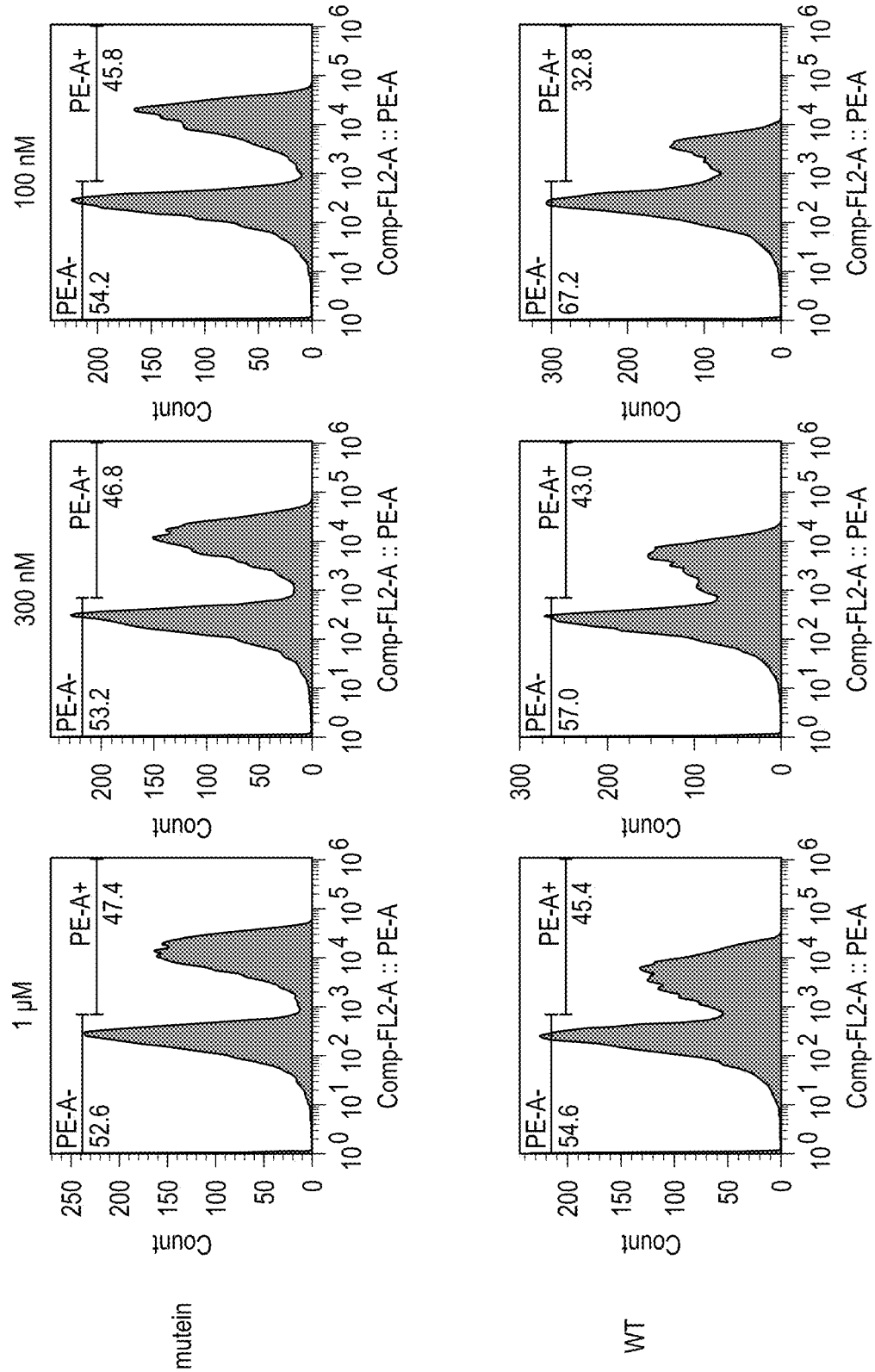
FIGS. 3A and 3B show yeast display selection of mutein of IL2. human IL-2 mutein, identified by yeast surface display screen, exhibits increased binding affinity to human IL-2R beta.
Figure 3A:
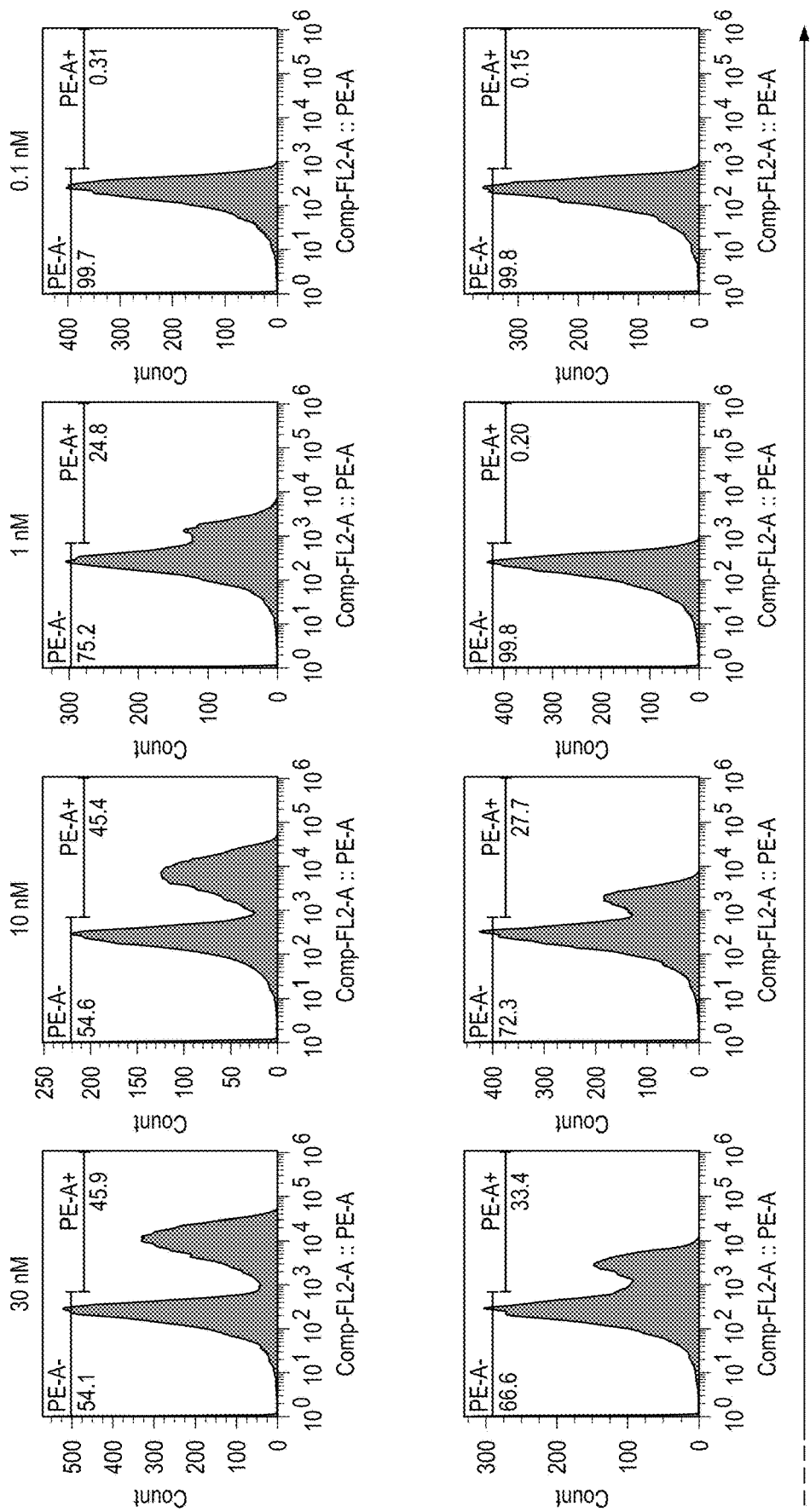
Figure 3B:
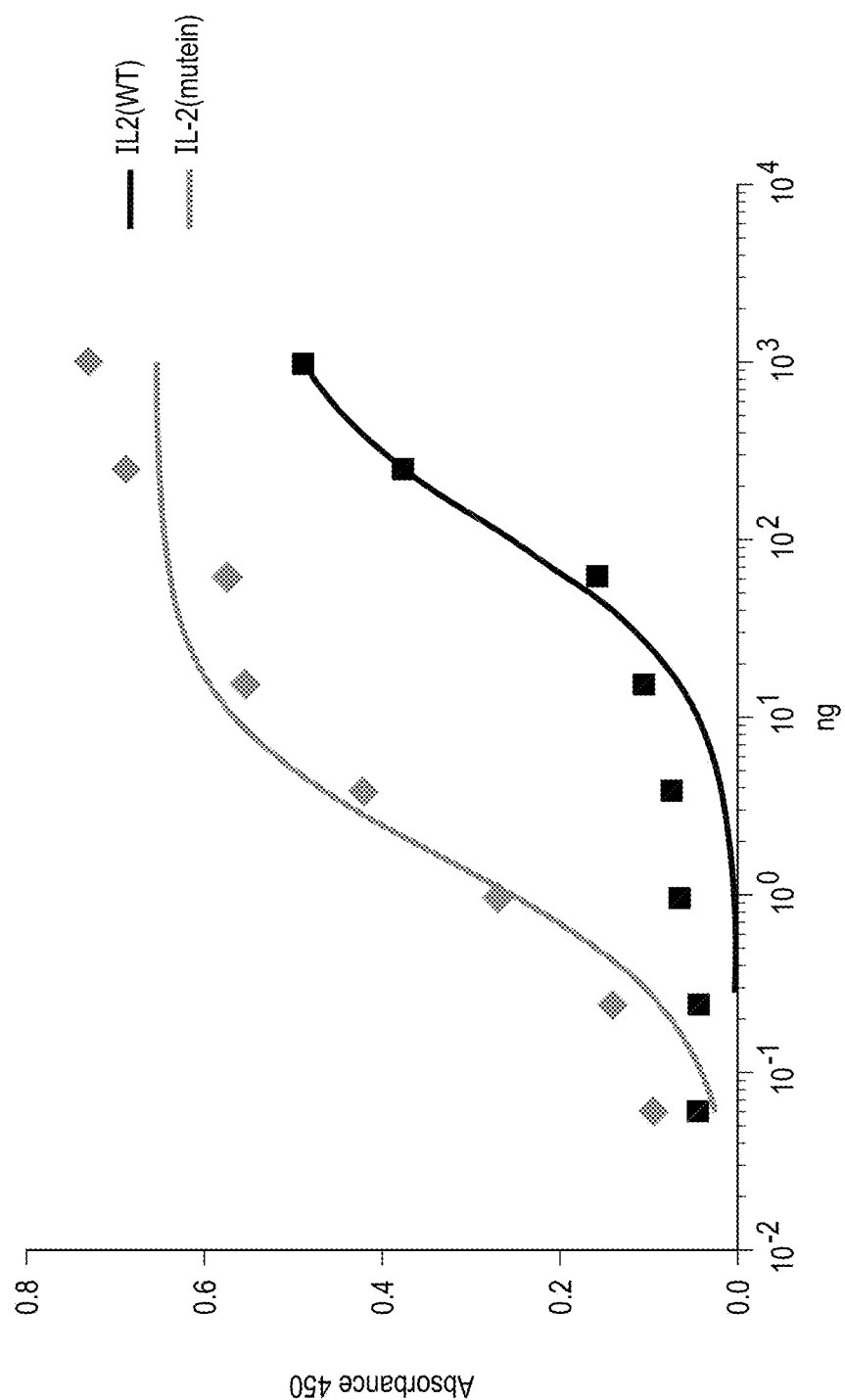

FIGS. 3A and 3B show yeast display selection of mutein of IL2. human IL-2 mutein, identified by yeast surface display screen, exhibits increased binding affinity to human IL-2R beta. (FIG. 3A) Flow cytometry data shows that IL-2R beta at a series of concentrations, binds to yeast expressing IL-2 mutein more strongly than IL-2 WT. (FIG. 3B) ELISA data shows that IL-2R beta binds to IL-2 mutein about 20 times stronger than IL-2 WT. The IL-2 mutein protein sequence is indicated in SEQ ID NO:3, but can also be any of SEQ ID NOS: 1-10.

Figure 4A:
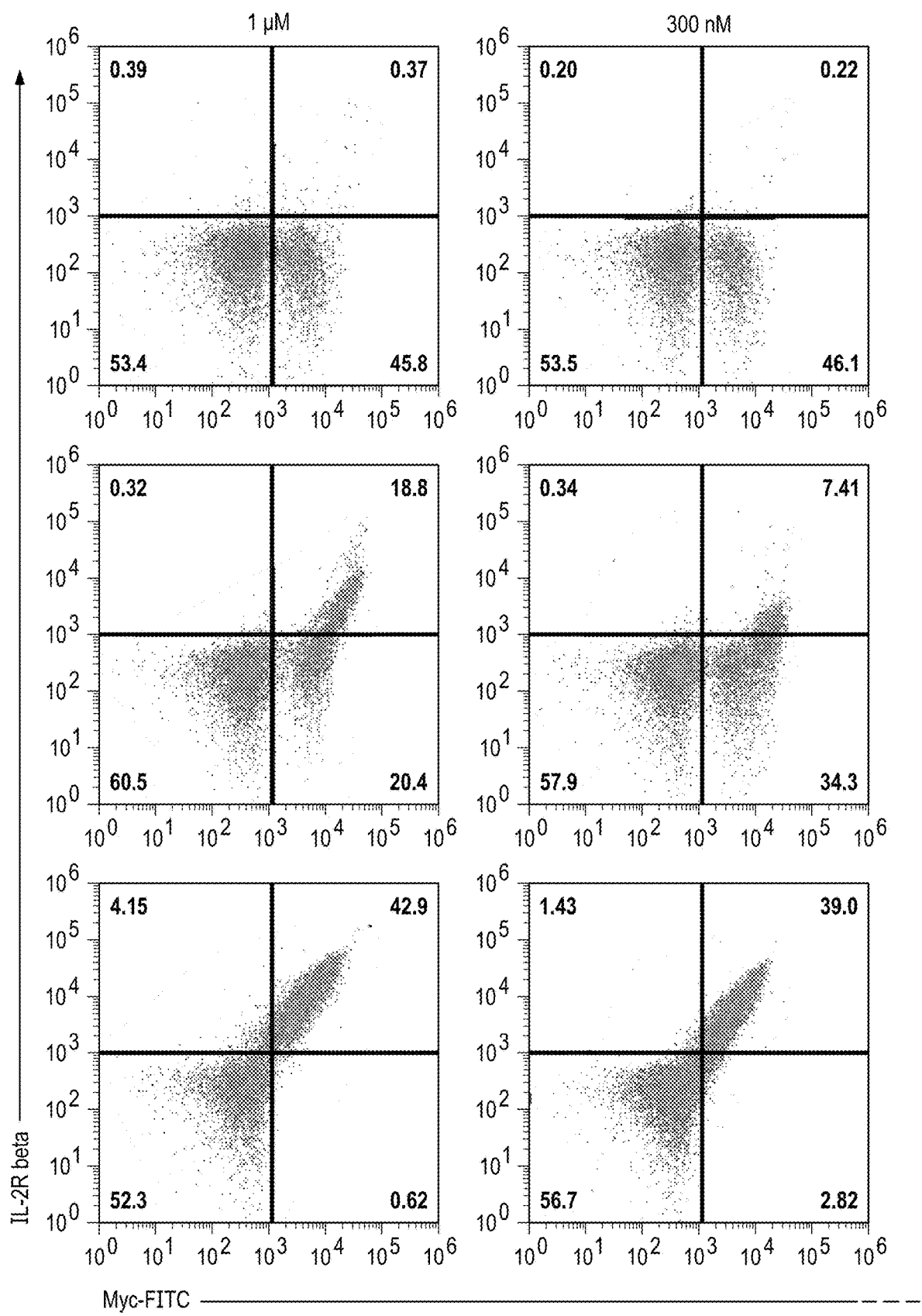
FIGS. 4A and 4B show the selection and identification of pH resistant IL2. human IL-2 muteins, identified by yeast surface display screen, exhibit stronger binding affinity to human IL-2R beta at pH 6.9 than WT protein.
Figure 4A:
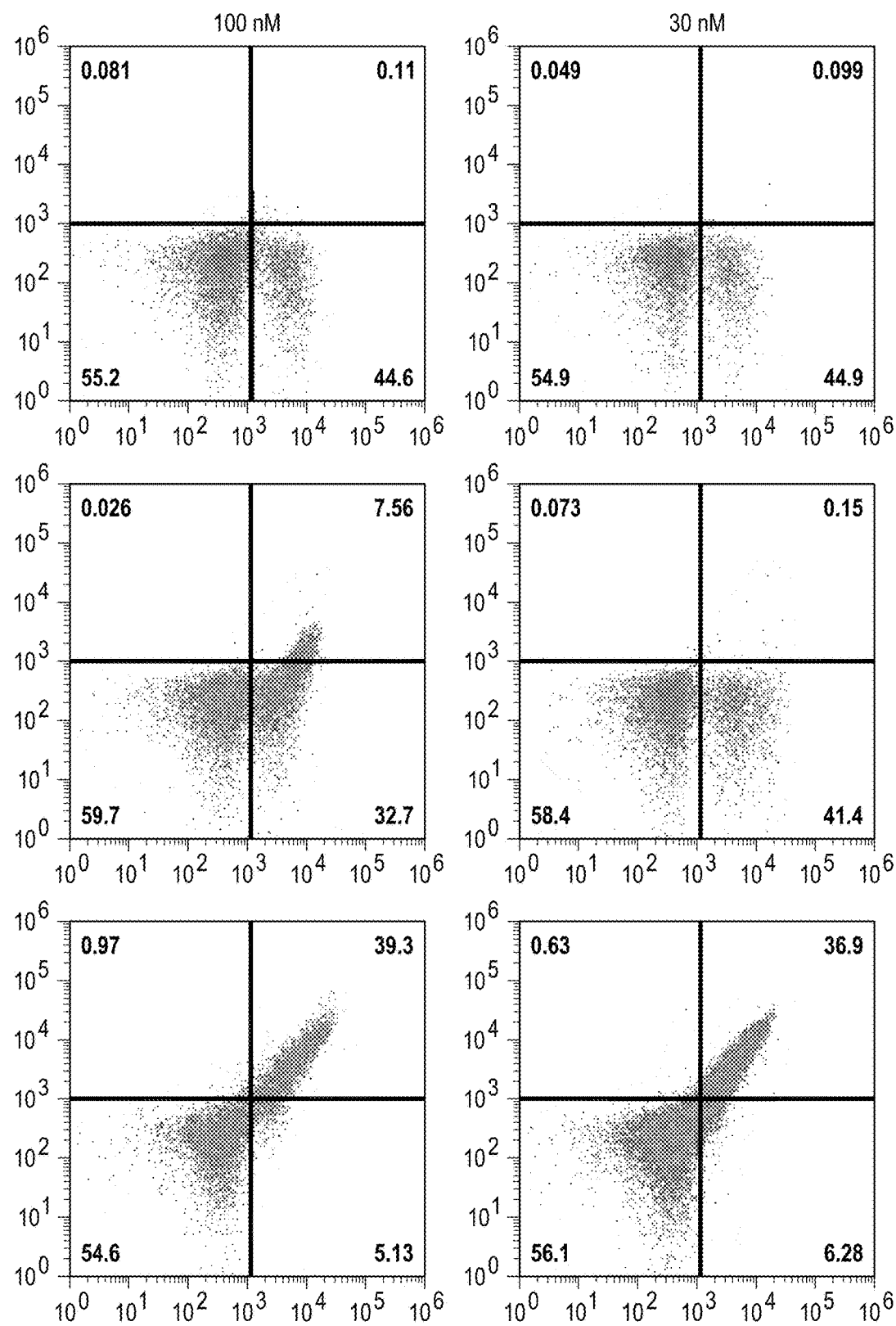
Figure 4A:
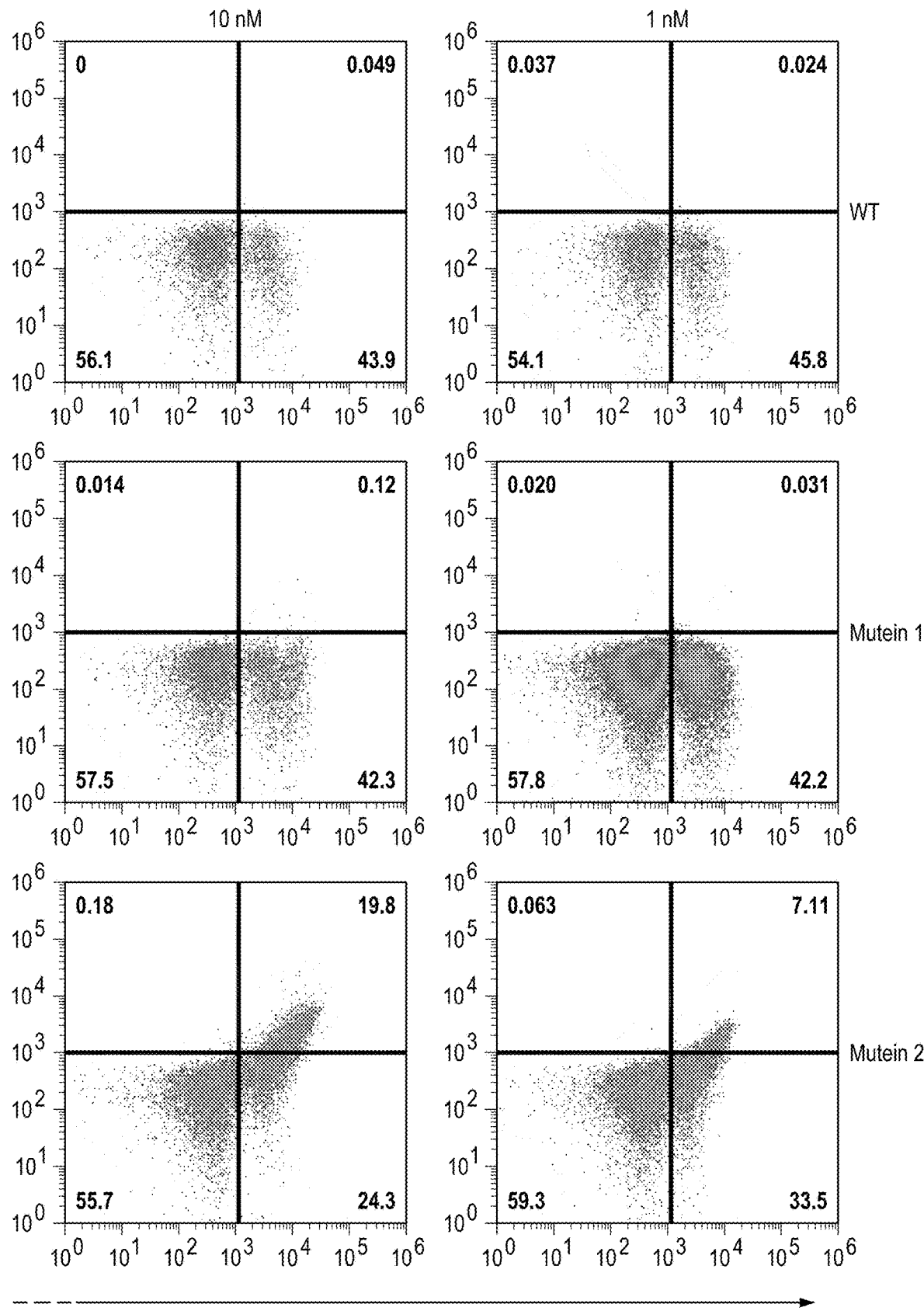
Figure 4B:
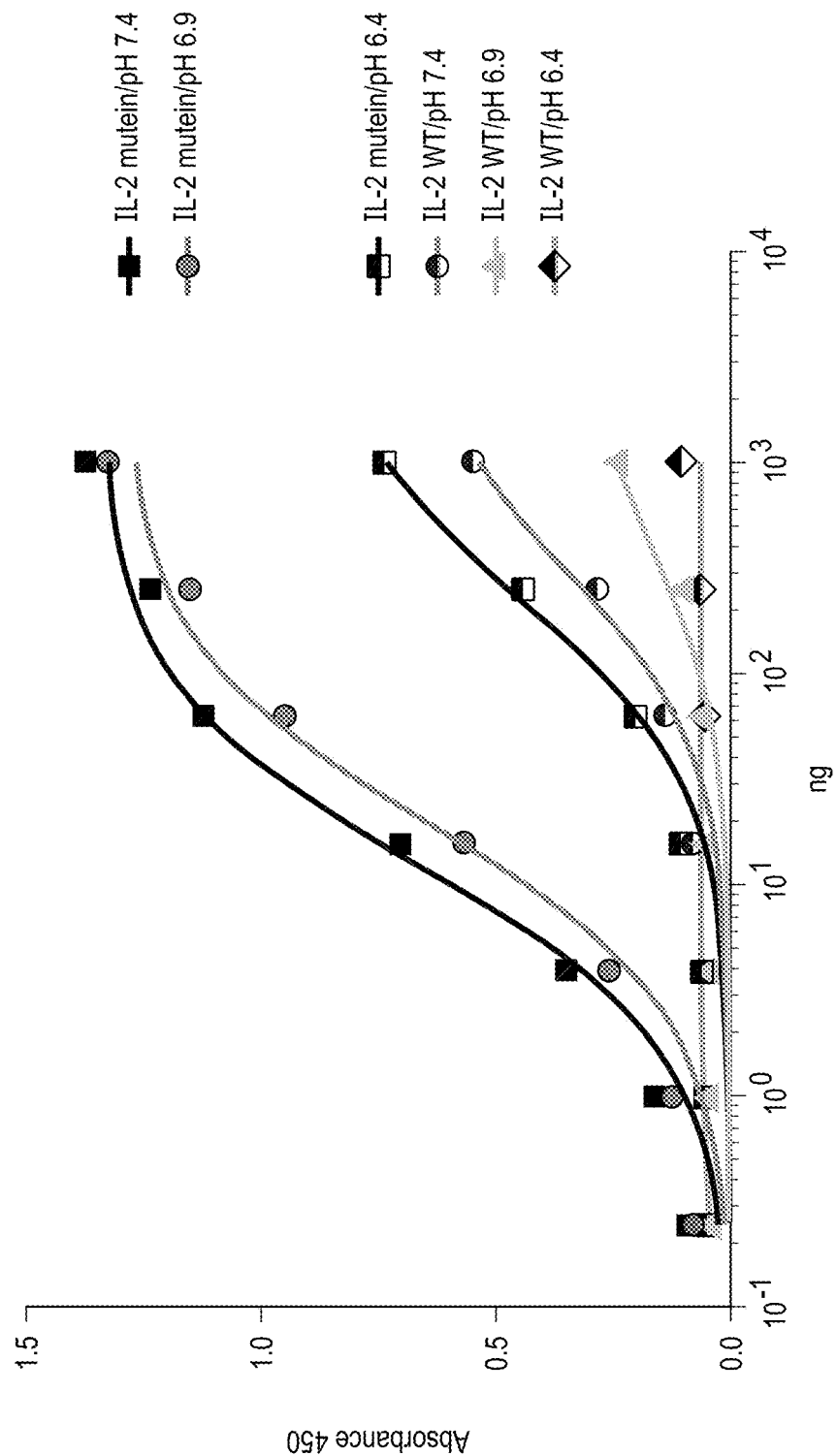

FIGS. 4A and 4B show the selection and identification of pH resistant IL2. human IL-2 muteins, identified by yeast surface display screen, exhibit stronger binding affinity to human IL-2R beta at pH 6.9 than WT protein. (FIG. 4A) Flow cytometry data shows that IL-2R beta at a series of concentrations, binds to yeast expressing IL-2 mutein more strongly than IL-2 WT at pH6.9. (FIG. 4B) ELISA data shows that IL-2R beta binds to IL-2 mutein, but not WT at pH 6.4, when both contains IL-2 mutein and WT contains F42A mutation to eliminate the binding to IL-2R alpha. The IL-2 mutein protein sequences are indicated in SEQ ID NOS:3-4, but can also be any of SEQ ID NOS: 1-10.

Figure 5A:
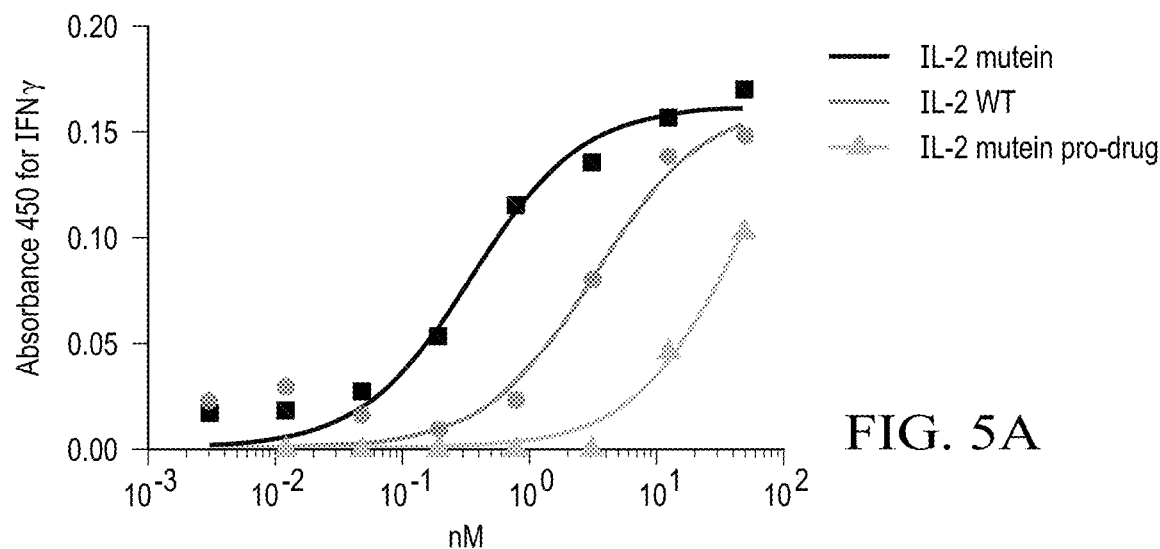
FIGS. 5A and 5B show human IL-2 mutein, identified by yeast surface display screen, more strongly activates human peripheral blood monocyte (HPBM) to produce IFN gamma.
Figure 5B:
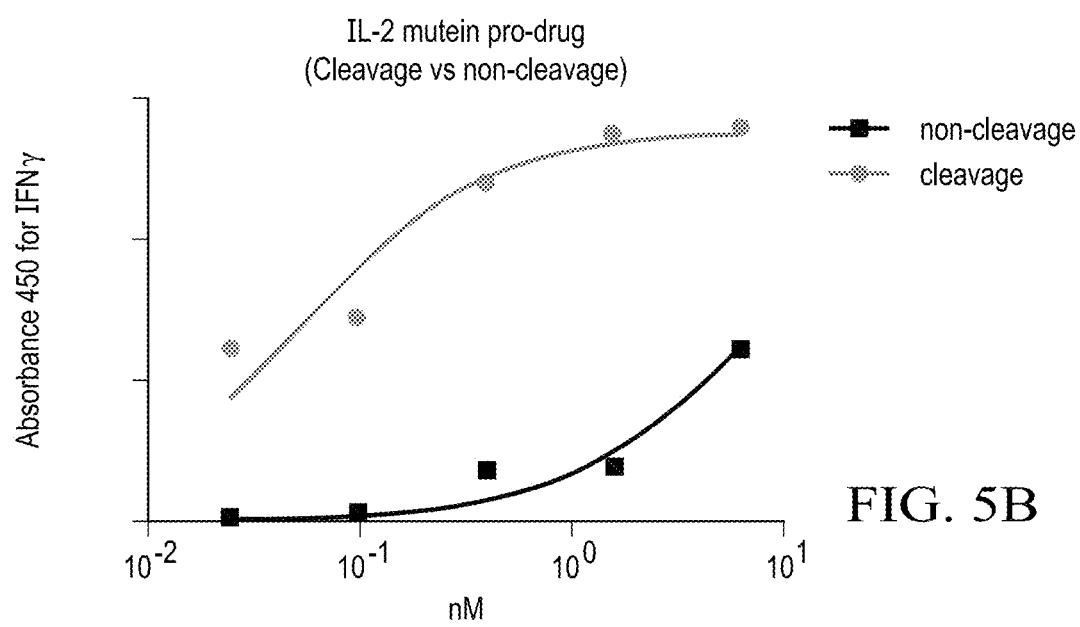

FIGS. 5A and 5B show human IL-2 mutein, identified by yeast surface display screen, more strongly activates human peripheral blood monocyte (HPBM) to produce IFN gamma. (FIG. 5A) ELISA data shows that IL-2 mutein induces human PBMC to produce IFN gamma about 10 times more strongly than IL-2 WT protein, when co-stimulated with anti-CD3 antibody. By contrast, the activity of IL-2 mutein pro-drug is more than 15 times lower than IL-2 WT, and more than 1000 times lower than IL-2 mutein. (FIG. 5B) ELISA data shows that IL-2 mutein pro-drug restores its activity to activate human PBMC for IFN gamma production after removal of the blocking moiety by incubating with MMP14 protein, when co-stimulated with anti-CD3 antibody. The IL-2 mutein protein sequence is indicated in SEQ ID NO:3, but can also be any of SEQ ID NOS: 1-10.

Figure 6:
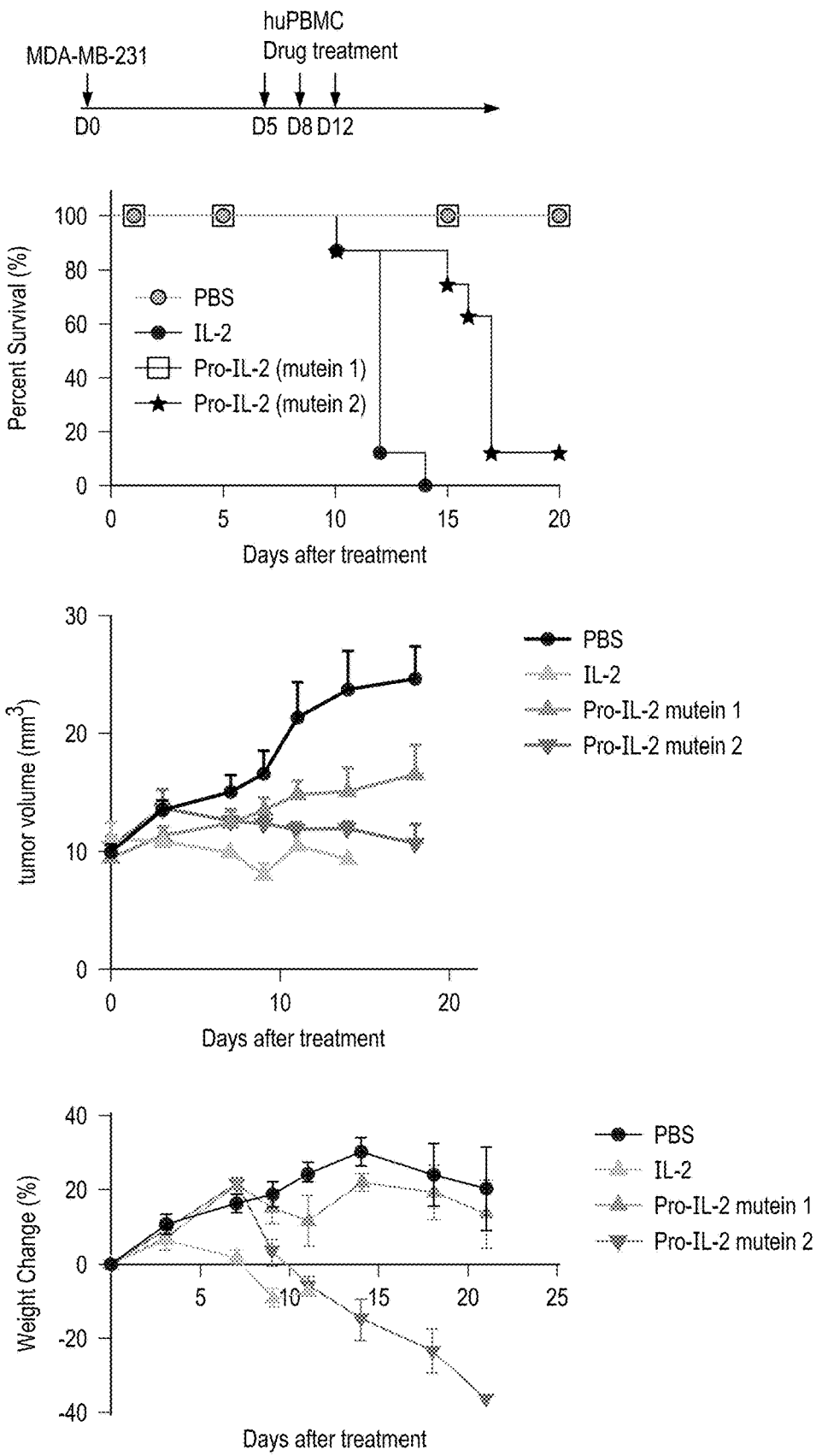
FIGS. 6 and 7 show target-binding polypeptide-fused IL-2 prodrug inhibits tumor growth in the mouse tumor model.
Figure 7:
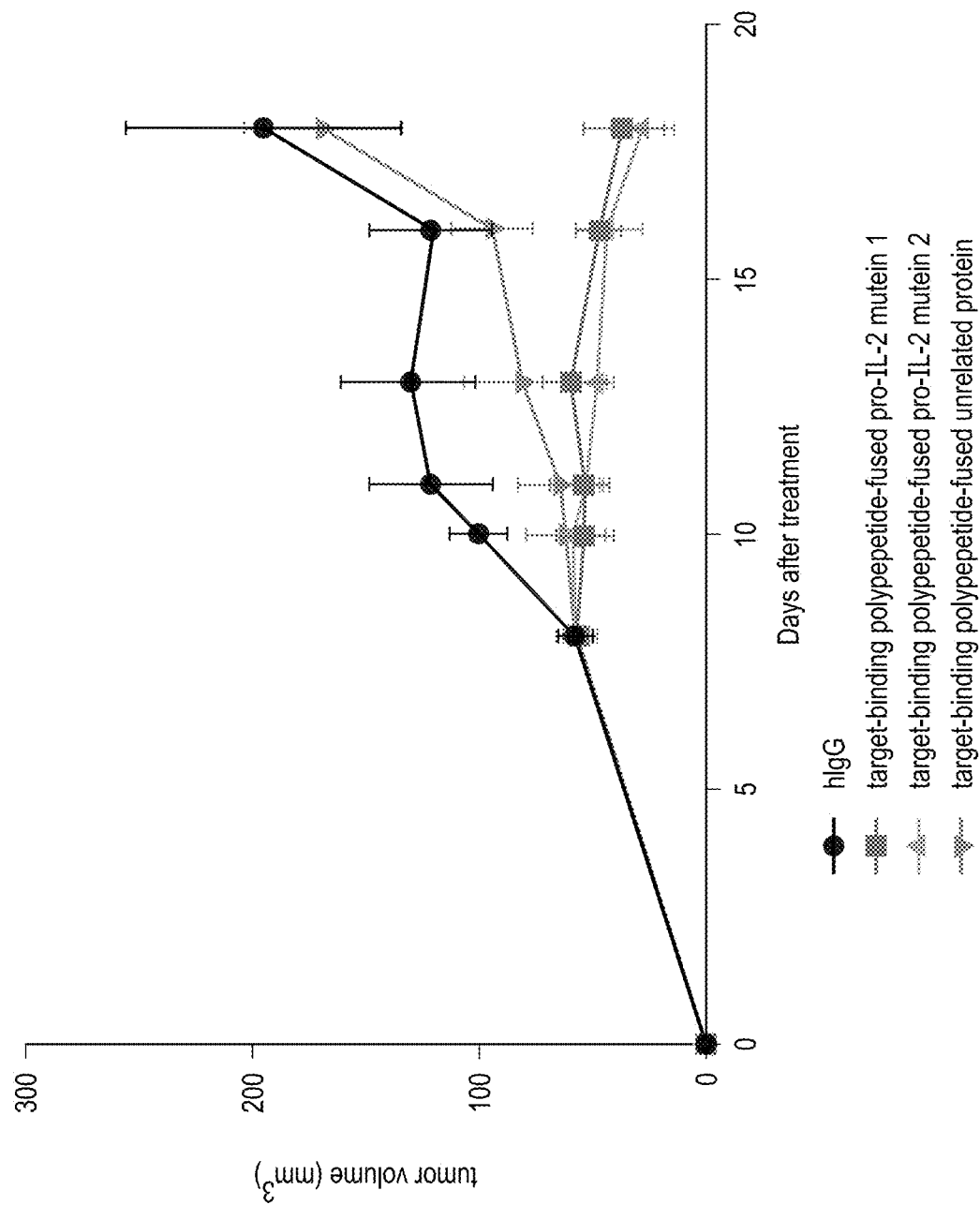

FIGS. 6 and 7 show target-binding polypeptide-fused IL-2 prodrug inhibits tumor growth in the mouse tumor model. (FIG. 6) pro-IL-2 mutein drug significantly inhibits tumor growth in the humanized mouse tumor model with mild body weight loss and improved survival, compared with IL-2 treatment. NSG-SGM3 mice inoculated with MDA-MB-231, followed by huPBMC transfer, and the treatment with IL-2 or pro-IL-2 mutein drugs. The IL-2 mutein protein sequences are indicated in SEQ ID NOS:3-4, but can also be any of SEQ ID NOS: 1-10. (FIG. 7) compared with hIgG and target-binding polypeptide-fused unrelated protein, target-binding polypeptide-fused IL-2 prodrug significantly inhibits tumor growth in mouse Antigen+M38 tumor model. The protein sequences of target-binding polypeptide-fused pro-IL-2 muteins are indicated in SEQ ID NOS:23-24.

Testing blocking of RB-pro-IL2.

The IL2 pro-drug, and the control (IL2-PSAcs-IL2R alpha), were incubated at various doses with HEK293 Blue IL2 reporter cells for 24 hours. Afterwards, color inducing reagents were incubated with the supernatant for 1 hour, and a spectrophotometer was used to quantify color to signify IL2 activity.

Testing IL2 prodrug in vivo.

For example, $10^6$ MC38 cells were injected subcutaneously into the right flank of C57BL/6 mice (n=4 per group). Mice were treated with PBS, 30 ug pro-IL2 drug, or 40 ug IL2-PSAcs-IL2R alpha intraperitoneally two times: on day 10 and 13 after tumor inoculation. Tumor volumes and body weight were measured on the noted days.

```
SEQ ID NO: 1: human IL-2 WT
APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT

SEQ ID NO: 2: human IL-2 mutant V0
APTSSSTKKTQLQLEHLLLDLQMILNGINNYKNPKLTRMLTAKFYMPKKA

TELKHLQCLEEELKPLEEVLNLAQSKNFHLRPRDLISNINVIVLELKGSE

TTFMCEYADETATIVEFLNRWITFCQSIISTLT

SEQ ID NO: 3: human IL-2 mutant V1
APTSSSTKKTQLQLEHLLLDLQMILNGINNYKNPKLTRMLTAKFYMPKKA

TELKHLQCLEEELKPLEEVLNLAQSKNFHLEPRDIISNINVIVLELKGSE

TTFMCEYADETATIVEFLNRWITFCQSIISTLT

SEQ ID NO: 4: human IL-2 mutant V2
APTSSSTKKTQLQLEHLLLDLQMILNGINNYKNPKLTRMLTAKFYMPKKA

TELKHLQCLEEELKPLEEVLNLAQSKNFHLEPRDTISNINVIVLELKGSE

TTFMCEYADETATIVEFLNRWITFCQSIISTLT

SEQ ID NO: 5: human IL-2 mutant V3
APTSSSTKKTQLQLEHLLLDLQMILNGINNYKNPKLTRMLTAKFYMPKKA

TELKHLQCLEEELKPLEEVLNLAQSKNFHLEPRDSISNINVIVLELKGSE

TTFMCEYADETATIVEFLNRWITFCQSIISTLT

SEQ ID NO: 6: human IL-2 mutant V4
APTSSSTKKTQLQLEHLLLDLQMILNGINNYKNPKLTRMLTAKFYMPKKA

TELKHLQCLEEELKPLEEVLNLAQSKNFHLDPRDEISNINVIVLELKGSE

TTFMCEYADETATIVEFLNRWITFCQSIISTLT

SEQ ID NO: 7: human IL-2 mutant V5
APTSSSTKKTQLQLEHLLLDLQMILNGINNYKNPKLTRMLTAKFYMPKKA

TELKHLQCLEEELKPLEEVLNLAQSKNFHLNPRDQISNINVIVLELKGSE

TTFMCEYADETATIVEFLNRWITFCQSIISTLT

SEQ ID NO: 8: human IL-2 mutant V6
APTSSSTKKTQLQLEHLLLDLQMILNGINNYKNPKLTRMLTAKFYMPKKA

TELKHLQCLEEELKPLEEVLNLAQSKNFHLDPRDQESNINVIVLELKGSE

TTFMCEYADETATIVEFLNRWITFCQSIISTLT

SEQ ID NO: 9: human IL-2 mutant V7
APTSSSTKKTQLQLEHLLLDLQMILNGINNYKNPKLTRMLTFKFYMPKKA

TELKHLQCLEEELKPLEEVLNLAQSKNFHLEPRDIISNINVIVLELKGSE

TTFMCEYADETATIVEFLNRWITFCQSIISTLT

SEQ ID NO: 10: human IL-2 mutant V8
APTSSSTKKTQLQLEHLLLDLQMILNGINNYKNPKLTRMLTFKFYMPKKA

TELKHLQCLEEELKPLEEVLNLAQSKNFHLEPRDTISNINVIVLELKGSE

TTFMCEYADETATIVEFLNRWITFCQSIISTLT

SEQ ID NO: 11: example of cleavable
Linker Sequence
SGRSENIRTA

SEQ ID NO: 12: example of cleavable
Linker Sequence
SGRSPAIFTA

SEQ ID NO: 13: example of cleavable
Linker Sequence
SGARYRWLTA

SEQ ID NO: 14: human IgG1 Fc (human Fc,
dimeric, wild-type)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK

SEQ ID NO: 15: human IgG1 Fc (human Fc,
dimeric, mutant)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK

SEQ ID NO: 16: human IgG1 Fc (human Fc,
monomeric, wild-type)
APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTKPPSRDELTKNQVSLSCLVKGFYPSDIAVE

WESNGQPENNYKTTVPVLDSDGSFRLASYLTVDKSRWQQGNVFSCSVMHE

ALHNHYTQKSLSLSPGK

SEQ ID NO: 17: human IgG1 Fc (human Fc,
monomeric, mutant)
APEAAGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALGA

PIEKTISKAKGQPREPQVYTKPPSRDELTKNQVSLSCLVKGFYPSDIAVE

WESNGQPENNYKTTVPVLDSDGSFRLASYLTVDKSRWQQGNVFSCSVMHE

ALHNHYTQKSLSLSPGK

SEQ ID NO: 18: human IgG1 Fc (human Fc6,
mutant)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVK

GFYPSDIAVEWESNGQPENNYKTTPPVLDSDGSFKLVSKLTVDKSRWQQG

NVFSCSVMHEALHNHYTQKSLSLSPGK
```

SEQ ID NO: 19: human IgG1 Fc (human Fc9, mutant)
DKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPCRDELTKNQVSLWCLVK
GFYPSDIAVEWESNGQPENNYKTTPPVLDSDGSFFLYSALTVDKSRWQQG
NVFSCSVMHEALHNHYTQKSLSLSPGK SEQ ID NO: 20: human IL-2R alpha extracellular domain
ELCDDDPPEIPHATFKAMAYKEGTMLNCECKRGFRRIKSGSLYMLCTGNS
SHSSWDNQCQCTSSATRNTTKQVTPQPEEQKERKTTEMQSPMQPVDQASL
PGHCREPPPWENEATERIYHFVVGQMVYYQCVQGYRALHRGPAESVCKMT
HGKTRWTQPQLICTGEMETSQFPGEEKPQASPEGRPESETSCLVTTTDFQ
IQTEMAATMETS SEQ ID NO: 21: human IL-2R beta extracellular domain
AVNGTSQFTCFYNSRANISCVWSQDGALQDTSCQVHAWPDRRRWNQTCEL
LPVSQASWACNLILGAPDSQKLTTVDIVTLRVLCREGVRWRVMAIQDFKP
FENLRLMAPISLQVVHVETHRCNISWEISQASHYFERHLEFEARTLSPGH
TWEEAPLLTLKQKQEWICLETLTPDTQYEFQVRVKPLQGEFTTWSPWSQP
LAFRTKPAALGKDT SEQ ID NO: 22: IgG kappa signal peptide
METDTLLLWVLLLWVPGSTGD SEQ ID NO: 23: Example of anti-Claudin-scFab-hFc$_{mu}$-IL2Rα-MMP14-IL2$_{wt}$
DIVMTQSPDSLAVSLGERATISCKSSQSLLNSGNQKNYLTWYQQKPGQPP
KLLIYWASTRESGVPDRFSGSGSGTDFTLTISSLQAEDVAVYYCQNDYFY
PFTFGQGTKLEIKRTVAAPSVFIFPPSDEQLKSGTASVVCLLNNFYPREA
KVQWKVDNALQSGNSQESVTEQDSKDSTYSLSSTLTLSKADYEKHKVYAC
EVTHQGLSSPVTKSFNRGECGSSGRSENIRTAGGSQVQLVQSGAEVKKPG
SSVKVSCKASGYAFSNYLIEWVKQAPGQGLEWIGLINPGSGGTNYNEKFK
GKATITADKSTSTAYMELSSLRSEDTAVYYCARVYYGNSFAYWGQGTLVT
VSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKR
VEPKSCEPKSSDKTHTCPPCPAPEAAGGPSVFLFPPKPKDTLMISRTPEV
TCVVVDVSHEDPEVKFNWYVDGVEVHNAKTKPREEQYNSTYRVVSVLTVL
HQDWLNGKEYKCKVSNKALGAPIEKTISKAKGQPREPQVYTLPPSRDELT
KNQVSLTCLVKGFYPSDIAVEWESNGQPENNYKTTPPVLDSDGSFFLYSK
LTVDKSRWQQGNVFSCSVMHEALHNHYTQKSLSLSPGKGGGGSGGGGSGG
GGSGGGGSAPTSSSTKKTQLQLEHLLLDLQMILNGINNYKNPKLTRMLTF
KFYMPKKATELKHLQCLEEELKPLEEVLNLAQSKNFHLRPRDLISNINVI
VLELKGSETTFMCEYADETATIVEFLNRWITFCQSIISTLTGGGGSGGGG
SSGARYRWLTAGGGGSGGGGSGGGGSELCDDDPPEIPHATFKAMAYKEGT
MLNCECKRGFRRIKSGSLYMLCTGNSSHSSWDNQCQCTSSATRNTTKQVT
PQPEEQKERKTTEMQSPMQPVDQASLPGHCREPPPWENEATERIYHFVVG
QMVYYQCVQGYRALHRGPAESVCKMTHGKTRWTQPQLICTGEMETSQFPG
EEKPQASPEGRPESETSCLVTTTDFQIQTEMAATMETS SEQ ID NO: 24: Example of anti-Claudin2-scFab-hF$_{mu}$-IL2Rα-MMP14-IL2$_{wt}$
DIVMTQSPSSLTVTAGEKVTMSCKSSQSLLNSGNQKNYLTWYQQKPGQPP
KLLIYWASTRESGVPDRFTGSGSGTDFTLTISSVQAEDLAVYYCQNDYSY
PFTFGSGTKLEIKRTVAAPSVFIFPPSDEQLKSGTASVVCLLNNFYPREA
KVQWKVDNALQSGNSQESVTEQDSKDSTYSLSSTLTLSKADYEKHKVYAC
EVTHQGLSSPVTKSFNRGECGSSGRSENIRTAGGSQVQLQQPGAELVRPG
ASVKLSCKASGYTFTSYWINWVKQRPGQGLEWIGNIYPSDSYTNYNQKFK
DKATLTVDKSSSTAYMQLSSPTSEDSAVYYCTRSWRGNSFDYWGQGTTLT
VSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKR
VEPKSCEPKSSDKTHTCPPCPAPEAAGGPSVFLFPPKPKDTLMISRTPEV
TCVVVDVSHEDPEVKFNWYVDGVEVHNAKTKPREEQYNSTYRVVSVLTVL
HQDWLNGKEYKCKVSNKALGAPIEKTISKAKGQPREPQVYTLPPSRDELT
KNQVSLTCLVKGFYPSDIAVEWESNGQPENNYKTTPPVLDSDGSFFLYSK
LTVDKSRWQQGNVFSCSVMHEALHNHYTQKSLSLSPGKGGGGSGGGGSGG
GGSGGGGSAPTSSSTKKTQLQLEHLLLDLQMILNGINNYKNPKLTRMLTF
KFYMPKKATELKHLQCLEEELKPLEEVLNLAQSKNFHLRPRDLISNINVI
VLELKGSETTFMCEYADETATIVEFLNRWITFCQSIISTLTGGGGSGGGG
SSGARYRWLTAGGGGSGGGGSGGGGSELCDDDPPEIPHATFKAMAYKEGT
MLNCECKRGFRRIKSGSLYMLCTGNSSHSSWDNQCQCTSSATRNTTKQVT
PQPEEQKERKTTEMQSPMQPVDQASLPGHCREPPPWENEATERIYHFVVG
QMVYYQCVQGYRALHRGPAESVCKMTHGKTRWTQPQLICTGEMETSQFPG
EEKPQASPEGRPESETSCLVTTTDFQIQTEMAATMETS When compared to WO 2016/022671, the present invention has the advantage that the IL2 mutein containing one or more mutations to reduce the binding to IL2R alpha (but not beta or gamma), activates the effector T cells in tumor microenvironment without activating regulatory T cells highly expressing receptor alpha. This has the potential to exhibit enhanced tumor-killing activity. The MMP14 cleavage sequence is embedded in the linker region which connects IL2R beta and IL2. This allows IL2R beta-mediated blockage in MMP14$^+$ tumors. Aside from the substitution of F42A in IL2 mutein, which decreases binding to receptor alpha, novel mutations are engineered to increase the binding to IL2 receptor beta and enhance the efficacy of prodrug. Also, the huFc region greatly increases the half-life of pro-drug, allows for convenient purification by affinity columns, and improves production stability. Finally, when using a Mutant Fc it is selected to not bind to FcR on phagocytes to reduce the depletion of effector cells.

When compared to U.S. Pat. No. 8,734,774, the present invention has the advantage that using an IL2 mutein, instead of wild type IL2, is used to abolish its binding to IL2R alpha, and can increase its efficacy to kill cancer cells as regulatory T cells are not activated in the tumor microenvironment. The huFc region is used to increase the half-life of pro-drug. MMP14 substrate sequence is used instead of substrates for MMP2 and MMP9, which are soluble. MMP14 may be a stronger selector for select solid tumors as it is a transmembrane protease demonstrated to be upregulated in some solid tumors. As IL2R-alpha is highly expressed in Treg, reduced binding to R-alpha will prevent the Treg engagement that is detrimental to anti-tumor effect of IL2, while the mutations that increase IL2 binding to IL2R-beta will address the problem that IL2 binds relatively weakly to IL2R-beta. In addition, for pro-drugs using IL-2R-alpha as a blocking moiety, the present invention has the advantage that using a half-life extender will significantly increase the prodrug half-life and improve its efficacy. More importantly, the present invention has fused target-binding polypeptides, which bind to tumor cell antigen, T cells, or tumor tissue-specific proteins specifically, and improve the pro-drug tumor targeting and reduce its toxicity.

When compared to WO 2020/057646 and WO 2020/057645, the present invention has the advantage that the fusion protein is a prodrug containing IL2 mutant protein and IL2R beta peptide to block the toxicity of IL2 mutant protein in periphery. Also, the MMP14 cleavage sequence is embedded in the linker region that connects IL2R beta and IL2. This allows IL2R beta-mediated blockage in MMP14-positive tumors.

In another embodiment, the present invention includes an activatable Interleukin-2 (aIL-2) fusion protein comprising, consisting essentially of, or consisting of: an Interleukin-2 (IL-2) wild type or IL-2 mutein; a first cleavable linker connected to the IL-2; an interleukin-2 receptor binding region (IL-2α or IL-2β receptor, interchangeable with IL-2RA or RB, respectively) connected to the first cleavable linker; and a half-life extender connected to the IL-2 or the IL-2 receptor, wherein cleavage of the cleavable linker releases the IL-2 from the IL-2 receptor. In one aspect, the half-life extender is an antibody Fc region, which is selected from: a wild-type Fc region, a mutated Fc region, a monomeric wild type Fc region, a monomeric mutant Fc region, a dimeric wild type Fc region, or a dimeric mutant Fc region. In another aspect, the cleavable linker is cleaved by a tumor associated protease. In another aspect, the cleavable linker is cleaved by a protease selected from matrix metallopeptidase-1 (MMP1), MMP2, MMP3, MMP7, MMP9, MMP10, MMP11, MMP12, MMP13, MMP14, MMP15, MMP16, MMP17, MMP19, MMP20, MMP21, uPA, FAPa, or Cathepsin B. In another aspect, the cleavable linker is cleaved by a caspase selected from Caspase 1, Caspase 2, Caspase 3, Caspase 4, Caspase 5, Caspase 6, Caspase 7, Caspase 8, Caspase 9, Caspase 10, Caspase 11 and Caspase 12. In another aspect, the cleavable linker is cleaved by matrix metallopeptidase 14. In another aspect, the IL-2 comprises one or more mutations that eliminate or reduce binding affinity to IL2RA or IL2RB. In another aspect, the IL-2 comprises one or more mutations selected from: F42A, K, R, E, or Q; Y45A, K, R, E, Q, F, W, or H; L72A, G, K, R, E, or Q; R81A, H, K, D, E, N, or Q; L85A, I, G, K, R, E, Q, T, or S; I86A, I, G, K, R, E, Q, T, or S. In another aspect, the IL-2 is mutated to increase binding affinity to IL2RB. In another aspect, the fusion protein is a homodimer. In another aspect, the fusion protein is a heterodimer. In another aspect, the fusion protein further comprises a target-binding polypeptide, wherein the target is selected from HER1, HER2, HER3, GD2, carcinoembryonic antigens (CEAs), epidermal growth factor receptor active mutant (EGFRVIII), CD133, Fibroblast Activation Protein Alpha (FAP), Epithelial cell adhesion molecular (Epcam), Glypican 3 (GPC3), EPH Receptor A4 (EphA), tyrosine-protein kinase Met (cMET), IL-13Ra2, microsomal epoxide hydrolase (mEH), MAGE, Mesothelin, MUC16, MUC1, prostate stem cell antigen (PSCA), Wilms tumor-1 (WT-1), a Claudin family protein; a T-cell marker selected from CTLA-4, PD-1, Lag3, S15, B7H3, B7H4, TCR-alpha, TCR-beta, TIM-3, CD3, 41BB or OX40; and/or an antigen-presenting cell marker selected from PD-L1, CD40, CD24, B7H3, TGF-beta receptor, TNFR family members 1 to 20, CD80, CD86, FLT3, CD11c, CD8-alpha, 5B6 (CLEC9A), CD1c, CD11b, CD13, CD33, HLA-DR, CD141, CD1a, CD32, CD45, CD80, CD86, CD207, CD2, CD7, CD45RA, CD68, CD123, CD303, CD304. In another aspect, the fusion protein reduces the in vivo toxicity of the aIL-2 when compared to IL-2. In another aspect, the fusion protein comprises, in order, the IL-2, the first cleavable linker, the IL-2 receptor, and a mutant antibody Fc region; the fusion protein comprises, in order, IL-2 receptor, the first cleavable linker, the IL-2, and the antibody Fc region; the fusion protein comprises, in order, the IL-2 or the IL-2 receptor, the first cleavable linker, the IL-2 or the IL-2 receptor, a second cleavable linker, and the antibody Fc region; the fusion protein comprises, in order, the antibody Fc region, the first cleavable linker, an IL-2 receptor, the second cleavable linker, and the IL-2; or the fusion protein comprises, in order, the antibody Fc region, the IL-2 receptor, the first cleavable linker, and the IL-2. In another aspect, the cleavable linker is a protease cleavable linker. In another aspect, the cleavable linker is cleaved by proteases upregulated during apoptosis or inflammation associated responses. In another aspect, the aIL-2 has a wild-type or mutant IL-2 selected from SEQ ID NOS: 1 to 10. In another aspect, the fusion protein comprises: (a) IL-2 is SEQ ID NOS: 1-10; (b) the IL-2Rα (SEQ ID NO:20) or the IL-2Rβ (SEQ ID NO: 21); (c) the cleavable linker is selected from SEQ ID NOS: 11-13, (d) human IgG1-Fc is SEQ ID NOS:14-19; and optionally a target-binding polypeptide. In another aspect, the aIL-2 has reduced toxicity in the heart, lungs, kidneys, or central nervous system when compared to IL-2. In another aspect, at least one of: the Interleukin-2 (IL-2); the first cleavable linker; the interleukin-2 receptor binding region (IL-2α or β receptor), or the antibody Fc region is a human sequence.

In another embodiment, the present invention includes a pharmaceutical composition comprising, consisting essentially of, or consisting of: an activatable Interleukin-2 (aIL-2) fusion protein comprising: an Interleukin-2 (IL-2) wild type or mutein; a first cleavable linker connected to the IL-2; an interleukin-2 receptor binding region (IL-2α or IL-2β receptor) connected to the first cleavable linker; and a half-life extender connected to the IL-2 or the IL-2 receptor, wherein cleavage of the cleavable linker releases the IL-2 from the IL-2 receptor and a carrier.

In another embodiment, the present invention includes a method of reducing binding activity of an activatable Interleukin-2 (aIL-2) against normal tissues and targeting a cancer cell comprising, consisting essentially of, or consisting of: administering an effective amount an activatable Interleukin-2 (aIL-2) fusion protein comprising: an Interleukin-2 (IL-2) wild type or mutein; a first cleavable linker connected to the IL-2; an interleukin-2 receptor binding region (IL-2α or IL-2β receptor) connected to the first cleavable linker; and a half-life extender connected to the IL-2 or the IL-2 receptor, wherein cleavage of the cleavable linker releases the IL-2 from the IL-2 receptor to a subject in need thereof.

In another embodiment, the present invention includes method of treating, alleviating a symptom of, or delaying the progression of a cancer comprising, consisting essentially of, or consisting of: administering an effective amount of the antibody of claim 1 to a subject in need thereof. In one aspect, the cancer is a cancer that expresses an enzyme that cleaves the cleavable linker. In another aspect, the cancer is selected from a bladder cancer, a bone cancer, a breast cancer, a carcinoid, a cervical cancer, a colon cancer, an endometrial cancer, a glioma, a head and neck cancer, a liver cancer, a lung cancer, a lymphoma, a melanoma, an ovarian cancer, a pancreatic cancer, a prostate cancer, a renal cancer, a sarcoma, a skin cancer, a stomach cancer, a testis cancer, a thyroid cancer, a urogenital cancer, or a urothelial cancer. In another aspect, the cancer is selected from the group consisting of: acute myeloid leukemia, adrenocortical carcinoma, B-cell lymphoma, bladder urothelial carcinoma, breast ductal carcinoma, breast lobular carcinoma, carcinomas of the esophagus, castration-resistant prostate cancer (CRPC), cervical carcinoma, cholangiocarcinoma, chronic myelogenous leukemia, colorectal adenocarcinoma, colorectal cancer (CRC), esophageal carcinoma, gastric adenocarcinoma, glioblastoma multiforme, head and neck squamous cell carcinoma, Hodgkin's lymphoma/primary mediastinal B-cell lymphoma, hepatocellular carcinoma (HCC), kidney chromophobe carcinoma, kidney clear cell carcinoma, kidney papillary cell carcinoma, lower grade glioma, lung adenocarcinoma, lung aquamous cell carcinoma, melanoma (MEL), mesothelioma, non-squamous NSCLC, ovarian serous adenocarcinoma, pancreatic ductal adenocarcinoma, paraganglioma & pheochromocytoma, prostate adenocarcinoma, renal cell carcinoma (RCC), sarcoma, skin cutaneous melanoma, squamous cell carcinoma of the head and neck, T-cell lymphoma, thymoma, thyroid papillary carcinoma, uterine carcinosarcoma, uterine corpus endometrioid carcinoma and uveal melanoma.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or. Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited features, elements, components, groups, integers, and/or steps, but do not exclude the presence of other unstated features, elements, components, groups, integers and/or steps. In embodiments of any of the compositions and methods provided herein, "comprising" may be replaced with "consisting essentially of" or "consisting of". As used herein, the term "consisting" is used to indicate the presence of the recited integer (e.g., a feature, an element, a characteristic, a property, a method/process step or a limitation) or group of integers (e.g., feature(s), element (s), characteristic(s), property(ies), method/process steps or limitation(s)) only. As used herein, the phrase "consisting essentially of" requires the specified features, elements, components, groups, integers, and/or steps, but do not exclude the presence of other unstated features, elements, components, groups, integers and/or steps as well as those that do not materially affect the basic and novel characteristic(s) and/or function of the claimed invention.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. An activatable Interleukin-2 (aIL-2) fusion protein comprising:
   an Interleukin-2 (IL-2) mutein comprising an R81E and L85T mutation;
   a first cleavable linker connected to the IL-2 mutein;
   an interleukin-2 receptor beta (IL-2R beta) binding region connected to the first cleavable linker; and
   a half-life extender connected to the IL-2 or the IL-2 receptor beta,
   wherein cleavage of the first cleavable linker releases the IL-2 mutein from the IL2-R beta, wherein the IL-2 mutein has increased binding affinity for IL-2R beta at pH 7.4 and retains binding to the IL-2R beta at pH 6.4.

2. The aIL-2 of claim 1, wherein the half-life extender is an antibody Fc region, which is selected from: a wild-type Fc region, a mutated Fc region, a monomeric wild type Fc region, a monomeric mutant Fc region, a dimeric wild type Fc region, or a dimeric mutant Fc region.

3. The aIL-2 of claim 1, wherein the first cleavable linker is cleaved by a tumor associated protease.

4. The aIL-2 of claim 1, wherein the first cleavable linker is cleaved by a protease selected from matrix metallopeptidase-1 (MMP1), MMP2, MMP3, MMP7, MMP9, MMP10, MMP11, MMP12, MMP13, MMP14, MMP15, MMP16, MMP17, MMP19, MMP20, MMP21, uPA, FAPa, or Cathepsin B.

5. The aIL-2 of claim 1, wherein the first cleavable linker is cleaved by a caspase selected from Caspase 1, Caspase 2, Caspase 3, Caspase 4, Caspase 5, Caspase 6, Caspase 7, Caspase 8, Caspase 9, Caspase 10, Caspase 11, or Caspase 12.

6. The aIL-2 of claim 1, wherein the first cleavable linker is cleaved by matrix metallopeptidase 14.

7. The aIL-2 of claim 1, wherein the fusion protein is a homodimer.

8. The aIL-2 of claim 1, wherein the fusion protein is a heterodimer.

9. The aIL-2 of claim 8, wherein the fusion protein further comprises a target-binding polypeptide, wherein the target is selected from HER1, HER2, HER3, GD2, carcinoembryonic antigens (CEAs), epidermal growth factor receptor active mutant (EGFR VIII), CD 133, Fibroblast Activation Protein Alpha (FAP), Epithelial cell adhesion molecular (Epcam), Glypican 3 (GPC3), EPH Receptor A4 (EphA), tyrosine-protein kinase Met (cMET), IL-13Ra2, microsomal epoxide hydrolase (mEH), MAGE, Mesothelin, MUC16, MUC1, prostate stem cell antigen (PSCA), Wilms tumor-1 (WT-1), a Claudin family protein; a T-cell marker selected from CTLA-4, PD-1, Lag3, S15, B7H3, B7H4, TCR-alpha, TCR-beta, TIM-3, CD3, 41BB or OX40; and/or an antigen-presenting cell marker selected from PD-L1, CD40, CD24, B7H3, TGF-beta receptor, TNFR family members 1 to 20, CD80, CD86, FLT3, CD11c, CD8-alpha, 5B6 (CLEC9A), CD1c, CD11b, CD13, CD33, HLA-DR, CD141, CD1a, CD32, CD45, CD80, CD86, CD207, CD2, CD7, CD45RA, CD68, CD123, CD303, or CD304.

10. The aIL-2 of claim 1, wherein the fusion protein reduces an in vivo toxicity of the aIL-2 when compared to IL-2.

11. The aIL-2 of claim 2, wherein the fusion protein comprises, in order, one of the following:
   the IL-2 mutein, the first cleavable linker, the IL-2 receptor beta, and the antibody Fc region;
   IL-2 receptor beta, the first cleavable linker, the IL-2 mutein, and the antibody Fc region;
   the IL-2 mutein or the IL-2 receptor beta, the first cleavable linker, the IL-2 mutein or the IL-2 receptor beta, a second cleavable linker, and the antibody Fc region;
   the antibody Fc region, the first cleavable linker, the IL-2 receptor beta, the second cleavable linker, and the IL-2 mutein; or
   the antibody Fc region, the IL-2 receptor beta, the first cleavable linker, and the IL-2 mutein.

12. The aIL-2 of claim 1, wherein the first cleavable linker is a protease cleavable linker.

13. The aIL-2 of claim 1, wherein the first cleavable linker is cleaved by proteases upregulated during apoptosis or an inflammatory response.

14. The aIL-2 of claim 1, wherein the IL-2 mutein is SEQ ID NO:4.

15. The aIL-2 of claim 1, wherein the aIL-2 has reduced toxicity in at least one of: heart, lung, kidney, or central nervous system when compared to IL-2.

16. The aIL-2 of claim 1, wherein at least one of: the IL-2 mutein; the first cleavable linker; the interleukin-2 receptor binding beta region, the half-life extender or an antibody Fc region, or an optional target-binding protein, is a human sequence.

17. A pharmaceutical composition comprising an aIL-2 of claim 1 and a carrier.

* * * * *

SEQUENCE LISTING

```
<160> NUMBER OF SEQ ID NOS: 24

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 2
<211> LENGTH: 133
<212> TYPE: PRT
<213> ORGANISM: Homo sapiens

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
```

```
                100                 105                 110
Thr Ile Val Glu Phe Leu Asn Arg Trp Ile Thr Phe Cys Gln Ser Ile
            115                 120                 125
Ile Ser Thr Leu Thr
            130

<210> SEQ ID NO 3
<211> LENGTH: 133
<212> TYPE: PRT
<213> ORGANISM: Homo sapiens

<400> SEQUENCE: 3

Ala Pro Thr Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Ala Lys Phe Tyr Met Pro Lys
            35                  40                  45
Lys Ala Thr Glu Leu Lys His Leu Gln Cys Leu Glu Glu Glu Leu Lys
        50                  55                  60
Pro Leu Glu Glu Val Leu Asn Leu Ala Gln Ser Lys Asn Phe His Leu
65                  70                  75                  80
Glu Pro Arg Asp Ile Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
            115                 120                 125
Ile Ser Thr Leu Thr
            130

<210> SEQ ID NO 4
<211> LENGTH: 133
<212> TYPE: PRT
<213> ORGANISM: Homo sapiens

<400> SEQUENCE: 4

Ala Pro Thr Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Ala Lys Phe Tyr Met Pro Lys
            35                  40                  45
Lys Ala Thr Glu Leu Lys His Leu Gln Cys Leu Glu Glu Glu Leu Lys
        50                  55                  60
Pro Leu Glu Glu Val Leu Asn Leu Ala Gln Ser Lys Asn Phe His Leu
65                  70                  75                  80
Glu Pro Arg Asp Thr Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
            115                 120                 125
Ile Ser Thr Leu Thr
            130
```

<210> SEQ ID NO 5
<211> LENGTH: 133
<212> TYPE: PRT
<213> ORGANISM: Homo sapiens

<400> SEQUENCE: 5

Ala Pro Thr Ser Ser Ser Thr Lys Lys Thr Gln Leu Gln Leu Glu His
1               5                   10                  15

Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Glu Pro Arg Asp Ser Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 6
<211> LENGTH: 133
<212> TYPE: PRT
<213> ORGANISM: Homo sapiens

<400> SEQUENCE: 6

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Asp Pro Arg Asp Glu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 7
<211> LENGTH: 133
<212> TYPE: PRT
<213> ORGANISM: Homo sapiens

<400> SEQUENCE: 7

Ala Pro Thr Ser Ser Ser Thr Lys Lys Thr Gln Leu Gln Leu Glu His
1               5                   10                  15

```
Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Asn Pro Arg Asp Gln Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr
        130

<210> SEQ ID NO 8
<211> LENGTH: 133
<212> TYPE: PRT
<213> ORGANISM: Homo sapiens

<400> SEQUENCE: 8

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Asp Pro Arg Asp Gln Glu Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr
        130

<210> SEQ ID NO 9
<211> LENGTH: 133
<212> TYPE: PRT
<213> ORGANISM: Homo sapiens

<400> SEQUENCE: 9

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60
```

Pro Leu Glu Glu Val Leu Asn Leu Ala Gln Ser Lys Asn Phe His Leu
65                  70                  75                  80

Glu Pro Arg Asp Ile Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 10
<211> LENGTH: 133
<212> TYPE: PRT
<213> ORGANISM: Homo sapiens

<400> SEQUENCE: 10

Ala Pro Thr Ser Ser Thr Lys Lys Thr Gln Leu Gln Leu Glu His
1                5                  10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Leu Lys
        50                  55                  60

Pro Leu Glu Glu Val Leu Asn Leu Ala Gln Ser Lys Asn Phe His Leu
65                  70                  75                  80

Glu Pro Arg Asp Thr Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 11
<211> LENGTH: 10
<212> TYPE: PRT
<213> ORGANISM: Artificial Sequence
<220> FEATURE:
<223> OTHER INFORMATION: Synthetic peptide

<400> SEQUENCE: 11

Ser Gly Arg Ser Glu Asn Ile Arg Thr Ala
1                5                  10

<210> SEQ ID NO 12
<211> LENGTH: 10
<212> TYPE: PRT
<213> ORGANISM: Artificial Sequence
<220> FEATURE:
<223> OTHER INFORMATION: Synthetic peptide

<400> SEQUENCE: 12

Ser Gly Arg Ser Pro Ala Ile Phe Thr Ala
1                5                  10

<210> SEQ ID NO 13

```
<211> LENGTH: 10
<212> TYPE: PRT
<213> ORGANISM: Artificial Sequence
<220> FEATURE:
<223> OTHER INFORMATION: Synthetic peptide

<400> SEQUENCE: 13

Ser Gly Ala Arg Tyr Arg Trp Leu Thr Ala
1               5                   10

<210> SEQ ID NO 14
<211> LENGTH: 227
<212> TYPE: PRT
<213> ORGANISM: Homo sapiens

<400> SEQUENCE: 14

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 15
<211> LENGTH: 227
<212> TYPE: PRT
<213> ORGANISM: Homo sapiens

<400> SEQUENCE: 15

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
```

```
                35                  40                  45
Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 16
<211> LENGTH: 217
<212> TYPE: PRT
<213> ORGANISM: Homo sapiens

<400> SEQUENCE: 16

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Lys Pro Pro Ser Arg Asp Glu Leu
        115                 120                 125

Thr Lys Asn Gln Val Ser Leu Ser Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Val Pro Val Leu Asp Ser Asp Gly Ser Phe Arg Leu
                165                 170                 175
```

```
Ala Ser Tyr Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 17
<211> LENGTH: 217
<212> TYPE: PRT
<213> ORGANISM: Homo sapiens

<400> SEQUENCE: 17

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Gly Ala Pro Ile Glu Lys Thr Ile Ser Lys Ala Lys Gly Gln
            100                 105                 110

Pro Arg Glu Pro Gln Val Tyr Thr Lys Pro Pro Ser Arg Asp Glu Leu
        115                 120                 125

Thr Lys Asn Gln Val Ser Leu Ser Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Val Pro Val Leu Asp Ser Asp Gly Ser Phe Arg Leu
                165                 170                 175

Ala Ser Tyr Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 18
<211> LENGTH: 227
<212> TYPE: PRT
<213> ORGANISM: Homo sapiens

<400> SEQUENCE: 18

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 19
<211> LENGTH: 227
<212> TYPE: PRT
<213> ORGANISM: Homo sapiens

<400> SEQUENCE: 19

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
            210                 215                 220
Pro Gly Lys
225

<210> SEQ ID NO 20
<211> LENGTH: 212
<212> TYPE: PRT
<213> ORGANISM: Homo sapiens

<400> SEQUENCE: 20

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
        50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
        130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
            195                 200                 205

Met Glu Thr Ser
        210

<210> SEQ ID NO 21
<211> LENGTH: 214
<212> TYPE: PRT
<213> ORGANISM: Homo sapiens

<400> SEQUENCE: 21

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

```
Arg Val Leu Cys Arg Glu Gly Val Arg Trp Arg Val Met Ala Ile Gln
            85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
            115                 120                 125

Ser Gln Ala Ser His Tyr Phe Glu Arg His Leu Glu Phe Glu Ala Arg
        130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
            195                 200                 205

Ala Leu Gly Lys Asp Thr
        210
```

<210> SEQ ID NO 22
<211> LENGTH: 21
<212> TYPE: PRT
<213> ORGANISM: Artificial Sequence
<220> FEATURE:
<223> OTHER INFORMATION: Synthetic peptide

<400> SEQUENCE: 22

```
Met Glu Thr Asp Thr Leu Leu Leu Trp Val Leu Leu Leu Trp Val Pro
1               5                   10                  15

Gly Ser Thr Gly Asp
            20
```

<210> SEQ ID NO 23
<211> LENGTH: 1088
<212> TYPE: PRT
<213> ORGANISM: Homo sapiens

<400> SEQUENCE: 23

```
Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro Phe Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140
```

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
    195                 200                 205

Ser Pro Val Thr Lys Ser Phe Asn Arg Gly Glu Cys Gly Ser Ser Gly
    210                 215                 220

Arg Ser Glu Asn Ile Arg Thr Ala Gly Gly Ser Gln Val Gln Leu Val
225                 230                 235                 240

Gln Ser Gly Ala Glu Val Lys Lys Pro Gly Ser Ser Val Lys Val Ser
            245                 250                 255

Cys Lys Ala Ser Gly Tyr Ala Phe Ser Asn Tyr Leu Ile Glu Trp Val
        260                 265                 270

Lys Gln Ala Pro Gly Gln Gly Leu Glu Trp Ile Gly Leu Ile Asn Pro
    275                 280                 285

Gly Ser Gly Gly Thr Asn Tyr Asn Glu Lys Phe Lys Gly Lys Ala Thr
290                 295                 300

Ile Thr Ala Asp Lys Ser Thr Ser Thr Ala Tyr Met Glu Leu Ser Ser
305                 310                 315                 320

Leu Arg Ser Glu Asp Thr Ala Val Tyr Tyr Cys Ala Arg Val Tyr Tyr
            325                 330                 335

Gly Asn Ser Phe Ala Tyr Trp Gly Gln Gly Thr Leu Val Thr Val Ser
        340                 345                 350

Ser Ala Ser Thr Lys Gly Pro Ser Val Phe Pro Leu Ala Pro Ser Ser
    355                 360                 365

Lys Ser Thr Ser Gly Gly Thr Ala Ala Leu Gly Cys Leu Val Lys Asp
    370                 375                 380

Tyr Phe Pro Glu Pro Val Thr Val Ser Trp Asn Ser Gly Ala Leu Thr
385                 390                 395                 400

Ser Gly Val His Thr Phe Pro Ala Val Leu Gln Ser Ser Gly Leu Tyr
            405                 410                 415

Ser Leu Ser Ser Val Val Thr Val Pro Ser Ser Ser Leu Gly Thr Gln
        420                 425                 430

Thr Tyr Ile Cys Asn Val Asn His Lys Pro Ser Asn Thr Lys Val Asp
    435                 440                 445

Lys Arg Val Glu Pro Lys Ser Cys Glu Pro Lys Ser Ser Asp Lys Thr
450                 455                 460

His Thr Cys Pro Pro Cys Pro Ala Pro Glu Ala Ala Gly Gly Pro Ser
465                 470                 475                 480

Val Phe Leu Phe Pro Pro Lys Pro Lys Asp Thr Leu Met Ile Ser Arg
            485                 490                 495

Thr Pro Glu Val Thr Cys Val Val Val Asp Val Ser His Glu Asp Pro
        500                 505                 510

Glu Val Lys Phe Asn Trp Tyr Val Asp Gly Val Glu Val His Asn Ala
    515                 520                 525

Lys Thr Lys Pro Arg Glu Glu Gln Tyr Asn Ser Thr Tyr Arg Val Val
    530                 535                 540

Ser Val Leu Thr Val Leu His Gln Asp Trp Leu Asn Gly Lys Glu Tyr
545                 550                 555                 560

Lys Cys Lys Val Ser Asn Lys Ala Leu Gly Ala Pro Ile Glu Lys Thr
```

-continued

```
                565                 570                 575
Ile Ser Lys Ala Lys Gly Gln Pro Arg Glu Pro Gln Val Tyr Thr Leu
            580                 585                 590

Pro Pro Ser Arg Asp Glu Leu Thr Lys Asn Gln Val Ser Leu Thr Cys
            595                 600                 605

Leu Val Lys Gly Phe Tyr Pro Ser Asp Ile Ala Val Glu Trp Glu Ser
            610                 615                 620

Asn Gly Gln Pro Glu Asn Asn Tyr Lys Thr Thr Pro Pro Val Leu Asp
625                 630                 635                 640

Ser Asp Gly Ser Phe Phe Leu Tyr Ser Lys Leu Thr Val Asp Lys Ser
            645                 650                 655

Arg Trp Gln Gln Gly Asn Val Phe Ser Cys Ser Val Met His Glu Ala
            660                 665                 670

Leu His Asn His Tyr Thr Gln Lys Ser Leu Ser Leu Ser Pro Gly Lys
            675                 680                 685

Gly Gly Gly Gly Ser Gly Gly Gly Ser Gly Gly Gly Gly Ser Gly
            690                 695                 700

Gly Gly Gly Ser Ala Pro Thr Ser Ser Ser Thr Lys Lys Thr Gln Leu
705                 710                 715                 720

Gln Leu Glu His Leu Leu Leu Asp Leu Gln Met Ile Leu Asn Gly Ile
            725                 730                 735

Asn Asn Tyr Lys Asn Pro Lys Leu Thr Arg Met Leu Thr Phe Lys Phe
            740                 745                 750

Tyr Met Pro Lys Lys Ala Thr Glu Leu Lys His Leu Gln Cys Leu Glu
            755                 760                 765

Glu Glu Leu Lys Pro Leu Glu Glu Val Leu Asn Leu Ala Gln Ser Lys
            770                 775                 780

Asn Phe His Leu Arg Pro Arg Asp Leu Ile Ser Asn Ile Asn Val Ile
785                 790                 795                 800

Val Leu Glu Leu Lys Gly Ser Glu Thr Thr Phe Met Cys Glu Tyr Ala
            805                 810                 815

Asp Glu Thr Ala Thr Ile Val Glu Phe Leu Asn Arg Trp Ile Thr Phe
            820                 825                 830

Cys Gln Ser Ile Ile Ser Thr Leu Thr Gly Gly Gly Ser Gly Gly
            835                 840                 845

Gly Gly Ser Ser Gly Ala Arg Tyr Arg Trp Leu Thr Ala Gly Gly Gly
            850                 855                 860

Gly Ser Gly Gly Gly Gly Ser Gly Gly Gly Gly Ser Glu Leu Cys Asp
865                 870                 875                 880

Asp Asp Pro Pro Glu Ile Pro His Ala Thr Phe Lys Ala Met Ala Tyr
            885                 890                 895

Lys Glu Gly Thr Met Leu Asn Cys Glu Cys Lys Arg Gly Phe Arg Arg
            900                 905                 910

Ile Lys Ser Gly Ser Leu Tyr Met Leu Cys Thr Gly Asn Ser Ser His
            915                 920                 925

Ser Ser Trp Asp Asn Gln Cys Gln Cys Thr Ser Ser Ala Thr Arg Asn
            930                 935                 940

Thr Thr Lys Gln Val Thr Pro Gln Pro Glu Glu Gln Lys Glu Arg Lys
945                 950                 955                 960

Thr Thr Glu Met Gln Ser Pro Met Gln Pro Val Asp Gln Ala Ser Leu
            965                 970                 975

Pro Gly His Cys Arg Glu Pro Pro Pro Trp Glu Asn Glu Ala Thr Glu
            980                 985                 990
```

```
Arg Ile Tyr His Phe Val Val Gly Gln Met Val Tyr Tyr Gln Cys Val
        995                 1000                1005

Gln Gly Tyr Arg Ala Leu His Arg Gly Pro Ala Glu Ser Val Cys
   1010                1015                1020

Lys Met Thr His Gly Lys Thr Arg Trp Thr Gln Pro Gln Leu Ile
   1025                1030                1035

Cys Thr Gly Glu Met Glu Thr Ser Gln Phe Pro Gly Glu Glu Lys
   1040                1045                1050

Pro Gln Ala Ser Pro Glu Gly Arg Pro Glu Ser Glu Thr Ser Cys
   1055                1060                1065

Leu Val Thr Thr Thr Asp Phe Gln Ile Gln Thr Glu Met Ala Ala
   1070                1075                1080

Thr Met Glu Thr Ser
   1085

<210> SEQ ID NO 24
<211> LENGTH: 1088
<212> TYPE: PRT
<213> ORGANISM: Homo sapiens

<400> SEQUENCE: 24

Asp Ile Val Met Thr Gln Ser Pro Ser Ser Leu Thr Val Thr Ala Gly
  1               5                  10                  15

Glu Lys Val Thr Met Ser Cys Lys Ser Ser Gln Ser Leu Leu Asn Ser
             20                  25                  30

Gly Asn Gln Lys Asn Tyr Leu Thr Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Tyr Pro Phe Thr Phe Gly Ser Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Gly Ser Ser Gly
    210                 215                 220

Arg Ser Glu Asn Ile Arg Thr Ala Gly Gly Ser Gln Val Gln Leu Gln
225                 230                 235                 240

Gln Pro Gly Ala Glu Leu Val Arg Pro Gly Ala Ser Val Lys Leu Ser
                245                 250                 255

Cys Lys Ala Ser Gly Tyr Thr Phe Thr Ser Tyr Trp Ile Asn Trp Val
```

```
            260                 265                 270
Lys Gln Arg Pro Gly Gln Gly Leu Glu Trp Ile Gly Asn Ile Tyr Pro
        275                 280                 285

Ser Asp Ser Tyr Thr Asn Tyr Asn Gln Lys Phe Lys Asp Lys Ala Thr
    290                 295                 300

Leu Thr Val Asp Lys Ser Ser Thr Ala Tyr Met Gln Leu Ser Ser
305                 310                 315                 320

Pro Thr Ser Glu Asp Ser Ala Val Tyr Tyr Cys Thr Arg Ser Trp Arg
                325                 330                 335

Gly Asn Ser Phe Asp Tyr Trp Gly Gln Gly Thr Thr Leu Thr Val Ser
            340                 345                 350

Ser Ala Ser Thr Lys Gly Pro Ser Val Phe Pro Leu Ala Pro Ser Ser
        355                 360                 365

Lys Ser Thr Ser Gly Gly Thr Ala Ala Leu Gly Cys Leu Val Lys Asp
    370                 375                 380

Tyr Phe Pro Glu Pro Val Thr Val Ser Trp Asn Ser Gly Ala Leu Thr
385                 390                 395                 400

Ser Gly Val His Thr Phe Pro Ala Val Leu Gln Ser Ser Gly Leu Tyr
                405                 410                 415

Ser Leu Ser Ser Val Val Thr Val Pro Ser Ser Ser Leu Gly Thr Gln
            420                 425                 430

Thr Tyr Ile Cys Asn Val Asn His Lys Pro Ser Asn Thr Lys Val Asp
        435                 440                 445

Lys Arg Val Glu Pro Lys Ser Cys Glu Pro Lys Ser Ser Asp Lys Thr
    450                 455                 460

His Thr Cys Pro Pro Cys Pro Ala Pro Glu Ala Ala Gly Gly Pro Ser
465                 470                 475                 480

Val Phe Leu Phe Pro Pro Lys Pro Lys Asp Thr Leu Met Ile Ser Arg
                485                 490                 495

Thr Pro Glu Val Thr Cys Val Val Val Asp Val Ser His Glu Asp Pro
            500                 505                 510

Glu Val Lys Phe Asn Trp Tyr Val Asp Gly Val Glu Val His Asn Ala
        515                 520                 525

Lys Thr Lys Pro Arg Glu Glu Gln Tyr Asn Ser Thr Tyr Arg Val Val
    530                 535                 540

Ser Val Leu Thr Val Leu His Gln Asp Trp Leu Asn Gly Lys Glu Tyr
545                 550                 555                 560

Lys Cys Lys Val Ser Asn Lys Ala Leu Gly Ala Pro Ile Glu Lys Thr
                565                 570                 575

Ile Ser Lys Ala Lys Gly Gln Pro Arg Glu Pro Gln Val Tyr Thr Leu
            580                 585                 590

Pro Pro Ser Arg Asp Glu Leu Thr Lys Asn Gln Val Ser Leu Thr Cys
        595                 600                 605

Leu Val Lys Gly Phe Tyr Pro Ser Asp Ile Ala Val Glu Trp Glu Ser
    610                 615                 620

Asn Gly Gln Pro Glu Asn Asn Tyr Lys Thr Thr Pro Pro Val Leu Asp
625                 630                 635                 640

Ser Asp Gly Ser Phe Phe Leu Tyr Ser Lys Leu Thr Val Asp Lys Ser
                645                 650                 655

Arg Trp Gln Gln Gly Asn Val Phe Ser Cys Ser Val Met His Glu Ala
            660                 665                 670

Leu His Asn His Tyr Thr Gln Lys Ser Leu Ser Leu Ser Pro Gly Lys
        675                 680                 685
```

```
Gly Gly Gly Gly Ser Gly Gly Gly Ser Gly Gly Gly Ser Gly
    690             695             700
Gly Gly Gly Ser Ala Pro Thr Ser Ser Thr Lys Lys Thr Gln Leu
705             710             715             720
Gln Leu Glu His Leu Leu Leu Asp Leu Gln Met Ile Leu Asn Gly Ile
            725             730             735
Asn Asn Tyr Lys Asn Pro Lys Leu Thr Arg Met Leu Thr Phe Lys Phe
            740             745             750
Tyr Met Pro Lys Lys Ala Thr Glu Leu Lys His Leu Gln Cys Leu Glu
            755             760             765
Glu Glu Leu Lys Pro Leu Glu Val Leu Asn Leu Ala Gln Ser Lys
770             775             780
Asn Phe His Leu Arg Pro Arg Asp Leu Ile Ser Asn Ile Asn Val Ile
785             790             795             800
Val Leu Glu Leu Lys Gly Ser Glu Thr Thr Phe Met Cys Glu Tyr Ala
            805             810             815
Asp Glu Thr Ala Thr Ile Val Glu Phe Leu Asn Arg Trp Ile Thr Phe
            820             825             830
Cys Gln Ser Ile Ile Ser Thr Leu Thr Gly Gly Gly Ser Gly Gly
            835             840             845
Gly Gly Ser Ser Gly Ala Arg Tyr Arg Trp Leu Thr Ala Gly Gly
850             855             860
Gly Ser Gly Gly Gly Ser Gly Gly Gly Ser Glu Leu Cys Asp
865             870             875             880
Asp Asp Pro Pro Glu Ile Pro His Ala Thr Phe Lys Ala Met Ala Tyr
            885             890             895
Lys Glu Gly Thr Met Leu Asn Cys Glu Cys Lys Arg Gly Phe Arg Arg
            900             905             910
Ile Lys Ser Gly Ser Leu Tyr Met Leu Cys Thr Gly Asn Ser Ser His
            915             920             925
Ser Ser Trp Asp Asn Gln Cys Gln Cys Thr Ser Ser Ala Thr Arg Asn
930             935             940
Thr Thr Lys Gln Val Thr Pro Gln Pro Glu Glu Gln Lys Glu Arg Lys
945             950             955             960
Thr Thr Glu Met Gln Ser Pro Met Gln Pro Val Asp Gln Ala Ser Leu
            965             970             975
Pro Gly His Cys Arg Glu Pro Pro Trp Glu Asn Glu Ala Thr Glu
            980             985             990
Arg Ile Tyr His Phe Val Val Gly Gln Met Val Tyr Tyr Gln Cys Val
            995             1000            1005
Gln Gly Tyr Arg Ala Leu His Arg Gly Pro Ala Glu Ser Val Cys
    1010            1015            1020
Lys Met Thr His Gly Lys Thr Arg Trp Thr Gln Pro Gln Leu Ile
    1025            1030            1035
Cys Thr Gly Glu Met Glu Thr Ser Gln Phe Pro Gly Glu Glu Lys
    1040            1045            1050
Pro Gln Ala Ser Pro Glu Gly Arg Pro Glu Ser Glu Thr Ser Cys
    1055            1060            1065
Leu Val Thr Thr Thr Asp Phe Gln Ile Gln Thr Glu Met Ala Ala
    1070            1075            1080
Thr Met Glu Thr Ser
    1085
```